United States Patent
Yoneda et al.

(10) Patent No.: US 10,760,115 B2
(45) Date of Patent: Sep. 1, 2020

(54) SPECIMEN DISRUPTING METHOD AND SPECIMEN DISRUPTING APPARATUS

(71) Applicants: FUJIFILM WAKO PURE CHEMICAL CORPORATION, Osaka (JP); FUJIFILM Techno Products Co., Ltd., Minamiashigara-shi, Kanagawa (JP)

(72) Inventors: Akito Yoneda, Amagasaki (JP); Tomohisa Kawabata, Amagasaki (JP); Yoichi Endo, Amagasaki (JP); Daisuke Hibe, Minamiashigara (JP); Mikio Tsuyuki, Minamiashigara (JP); Tatsuyuki Denawa, Minamiashigara (JP)

(73) Assignee: FUJIFILM WAKO PURE CHEMICAL CORPORATION, Osaka (JP)

( * ) Notice: Subject to any disclaimer, the term of this patent is extended or adjusted under 35 U.S.C. 154(b) by 664 days.

(21) Appl. No.: 15/527,153

(22) PCT Filed: Nov. 17, 2015

(86) PCT No.: PCT/JP2015/005740
§ 371 (c)(1),
(2) Date: May 16, 2017

(87) PCT Pub. No.: WO2016/079981
PCT Pub. Date: May 26, 2016

(65) Prior Publication Data
US 2017/0335372 A1  Nov. 23, 2017

(30) Foreign Application Priority Data
Nov. 18, 2014 (JP) .................... 2014-233365

(51) Int. Cl.
*C12Q 1/6806* (2018.01)
*G01N 1/28* (2006.01)
(Continued)

(52) U.S. Cl.
CPC ............ *C12Q 1/6806* (2013.01); *B01F 9/002* (2013.01); *B01F 9/0005* (2013.01);
(Continued)

(58) Field of Classification Search
CPC ....... C12Q 1/6806; C12M 47/06; C12M 1/00; B02C 17/06; B02C 17/08; B02C 25/00;
(Continued)

(56) References Cited

U.S. PATENT DOCUMENTS 5,578,269 A * 11/1996 Yaremko .............. G01N 35/025
  210/361
6,162,399 A * 12/2000 Martinell Gisper-Sauch ..............
  G01N 35/0099
  422/63

(Continued)

FOREIGN PATENT DOCUMENTS

| CN | 1333666 A | 1/2002 |
| CN | 103718012 A | 4/2014 |

(Continued)

OTHER PUBLICATIONS

Written Opinion of the International Searching Authority of PCT/JP2015/005740 dated Mar. 8, 2016.
(Continued)

*Primary Examiner* — Faye Francis
*Assistant Examiner* — Smith Oberto Bapthelus
(74) *Attorney, Agent, or Firm* — Sughrue Mion, PLLC

(57) ABSTRACT

A specimen disrupting apparatus includes: a drive unit that rotates the lower portion of a container having a solution that includes a specimen, a great number of small diameter
(Continued)

beads, and a large diameter bead stored therein; and a control unit that controls the drive unit. The control unit controls the drive unit such that the lower portion of the container rotates at two or more different rotational speeds which are changed continuously.

17 Claims, 14 Drawing Sheets

(51) Int. Cl.
| | |
|---|---|
| *B02C 17/06* | (2006.01) |
| *B02C 17/08* | (2006.01) |
| *C12M 1/00* | (2006.01) |
| *B01F 9/00* | (2006.01) |
| *B01F 13/00* | (2006.01) |
| *B02C 25/00* | (2006.01) |

(52) U.S. Cl.
CPC .......... *B01F 13/0052* (2013.01); *B02C 17/06* (2013.01); *B02C 17/08* (2013.01); *B02C 25/00* (2013.01); *C12M 47/06* (2013.01); *G01N 1/28* (2013.01); *G01N 1/286* (2013.01); *C12M 1/00* (2013.01); *G01N 2001/2866* (2013.01)

(58) Field of Classification Search
CPC .. G01N 1/28; G01N 1/286; G01N 2001/2866; B01F 13/0052; B01F 9/002; B01F 9/0005
USPC .......................................................... 241/22
See application file for complete search history.

(56) References Cited

U.S. PATENT DOCUMENTS

| | | | | |
|---|---|---|---|---|
| 9,186,677 | B2 * | 11/2015 | Williams | B01L 3/5027 |
| 9,802,199 | B2 * | 10/2017 | Handique | G01N 21/6428 |
| 9,963,670 | B2 * | 5/2018 | Boos | G01N 1/286 |
| 10,413,130 | B2 * | 9/2019 | Vu | A47J 43/046 |
| 2004/0248130 | A1 * | 12/2004 | Osanai | C12N 15/1003 |
| | | | | 435/6.15 |
| 2006/0158956 | A1 * | 7/2006 | Laugharn, Jr. | B01F 11/02 |
| | | | | 366/127 |
| 2006/0175443 | A1 * | 8/2006 | Bysouth | B01F 9/0001 |
| | | | | 241/30 |
| 2008/0223962 | A1 | 9/2008 | Kemppainen et al. | |
| 2008/0262605 | A1 * | 10/2008 | Dancu | G09B 23/28 |
| | | | | 623/1.41 |
| 2009/0134069 | A1 * | 5/2009 | Handique | B01L 9/527 |
| | | | | 209/11 |
| 2009/0221059 | A1 * | 9/2009 | Williams | B01L 3/5027 |
| | | | | 435/287.2 |
| 2010/0098584 | A1 * | 4/2010 | Kobayashi | G01N 35/025 |
| | | | | 422/64 |
| 2011/0070589 | A1 | 3/2011 | Belgrader et al. | |
| 2011/0086780 | A1 * | 4/2011 | Colston, Jr. | B01F 3/0807 |
| | | | | 506/23 |
| 2011/0250617 | A1 * | 10/2011 | Delafosse | B01L 3/5021 |
| | | | | 435/7.2 |
| 2012/0088269 | A1 | 4/2012 | Kusumegi et al. | |
| 2013/0126436 | A1 * | 5/2013 | Ok | B03C 1/30 |
| | | | | 210/695 |
| 2013/0217010 | A1 * | 8/2013 | Suchocki | B01F 13/0052 |
| | | | | 435/6.11 |
| 2013/0288355 | A1 * | 10/2013 | DeWitte | G01N 30/06 |
| | | | | 435/288.6 |
| 2014/0117131 | A1 | 5/2014 | Gouko et al. | |
| 2014/0242678 | A1 * | 8/2014 | Boos | G01N 1/286 |
| | | | | 435/259 |
| 2016/0032358 | A1 * | 2/2016 | Buse | C12Q 1/686 |
| | | | | 435/6.12 |
| 2017/0335372 | A1 * | 11/2017 | Yoneda | G01N 1/28 |

FOREIGN PATENT DOCUMENTS

| | | |
|---|---|---|
| JP | 2002-000255 A | 1/2002 |
| JP | 2006-141292 A | 6/2006 |
| JP | 2009-011210 A | 1/2009 |
| JP | 2006141292 * | 1/2009 |
| JP | 2010-249683 A | 11/2010 |
| JP | 2011-19488 A | 2/2011 |
| JP | 2014-002107 A | 1/2014 |
| JP | 5542379 B2 | 7/2014 |
| JP | 2014-525041 A | 9/2014 |
| WO | 2010/147111 A1 | 12/2010 |

OTHER PUBLICATIONS

International Search Report of PCT/JP2015/005740 dated Mar. 8, 2016.
Communication dated May 8, 2019, from the China National Intellectual Property Administration in counterpart Application No. 201580061356.9.
Extended European Search Report dated Oct. 23, 2017 issued by the European Patent Office in counterpart application No. 15860310.0.
Communication dated Dec. 3, 2019 by China National Intellectual Property Administration in application No. 201580061356.9.

* cited by examiner

US 10,760,115 B2

SPECIMEN DISRUPTING METHOD AND SPECIMEN DISRUPTING APPARATUS

CROSS REFERENCE TO RELATED APPLICATIONS

The present application is a National Phase Entry of PCT International Application No. PCT/JP2015/005740 filed on Nov. 17, 2015, which claims priority under 35 U.S.C. § 119(a) to Japanese Patent Application No. 2014-233365 filed on Nov. 18, 2014. Each of the above applications is hereby expressly incorporated by reference, in its entirety, into the present application.

TECHNICAL FIELD

The present disclosure is related to a specimen disrupting method and a specimen disrupting apparatus. More particularly, the present disclosure relates to a disrupting apparatus for storing a solution containing a specimen, such as a bacterial cell or a virus, and beads in a container, causing the stored container to rotate, and then subjecting the specimen to physical impact by the beads, thereby disrupting the specimens.

BACKGROUND ART

In recent years, genetic diagnosis has attracted focus accompanying the development of life sciences. In genetic diagnosis, specimens such as bacterial cells or viruses are disrupted and nucleic acids such as DNA (Deoxyribonucleic Acid) and RNA (Ribonucleic Acid) are extracted from the interiors thereof. The extracted nucleic acids are purified, then amplified by the PCR (Polymerase Chain Reaction) method or the like, and analyzed by the electrophoresis method or the like.

As described above, in genetic diagnosis, it is necessary to disrupt specimens as a pretreatment to a degree that the nucleic acids are not broken. Various methods are known for disruption processing of such specimens. There is known a technique in which a solution containing a specimen and a proteolytic enzyme are stored in a container, and the lower portion of the storage container is eccentrically rotated to agitate the solution and the proteolytic enzyme, to disrupt the specimen (Japanese Unexamined Patent Publication No. 2002-255).

In addition, a technique in which a container is eccentrically rotated in a state where the central axis of the container and the rotational axis are parallel is also known (Japanese Patent No. 5542379). Further, there is a known method in which a surfactant is mixed into a specimen to disrupt the specimen.

However, in the disruption effected by chemical treatment described above, there is a possibility that cell walls will not be sufficiently broken. Therefore, a technique has been proposed in which a solution containing a specimen, a great number of small diameter beads, and a large diameter bead are stored in a container, and the container is agitated to impart physical impact by the beads to the specimen to disrupt the specimen (Japanese Unexamined Patent Publication No. 2006-141292).

SUMMARY

Technical Problem

However, in genetic diagnosis, it is also required to disrupt a large number of specimens collected from animals (mainly humans) and plants in a short period of time in order to increase diagnostic efficiency. The technique proposed in Japanese Unexamined Patent Publication No. 2006-141292 merely discloses the use of a great number of small diameter beads and a large diameter bead to disrupt the specimen, and is silent regarding how diagnostic efficiency is improved by using such beads.

The present disclosure has been developed in view of the foregoing circumstances. The present disclosure provides a method and an apparatus for rotating a container storing a specimen, a great number of small diameter beads, and a large diameter bead, to disrupt the specimen, which is capable of disrupting the specimen efficiently and in a short amount of time.

A specimen disrupting apparatus according to the present disclosure comprises:

a drive unit configured to cause a lower portion of a container containing a solution which includes a specimen, a great number of small diameter beads and a large diameter bead to rotate; and a control unit configured to control the drive unit;

the control unit controlling the drive unit such that the lower portion of the container rotates at two or more different rotational speeds which change continuously.

A specimen disrupting method according to the present disclosure comprises:

storing a solution containing a specimen, a great number of small diameter beads, and a large diameter bead in a container; and causing a lower portion of the container to rotate while continuously changing the rotational speed among two or more different rotational speeds, to disrupt the specimen with the beads.

Here, the above "great number of small diameter beads" means that from 10 to 50,000, preferably from 1,000 to 10,000, and more preferably from 5,000 to 10,000 beads having diameters within a range from approximately 0.1 mm to 1 mm are present within the container. The above "large diameter bead" refers to a bead having a diameter which is greater than the diameters of the small diameter beads by a factor of approximately 10 to 100. The diameter of the large diameter bead is within a range from 1 to 10 mm, and preferably within a range from 3 to 8 mm.

In the specimen disrupting apparatus and method of the present disclosure, it is desirable for the minimum rotational speed to be within a range from 1000 rpm to 4000 rpm and for the maximum rotational speed to be within a range from 5000 rpm to 9000 rpm, among the two or more different rotational speeds at which the lower portion of the container is rotated. The term "rpm" is an abbreviation for "revolution per minute".

Further, in the specimen disrupting apparatus of the present disclosure, it is preferable for the container to comprise a rib at the upper portion of the inner circumferential surface thereof that causes the small diameter beads to bounce upward from the inner circumferential surface. Also, it is desirable for the inner circumferential surface at the lower portion of the container to be smooth such that the large diameter bead rolls on the lower inner circumferential surface during rotation.

Further, in the specimen disrupting method according to the present disclosure, it is desirable for the large diameter beads to be rolled on the inner circumferential surface at the lower portion of the container, and for the small diameter beads to be moved in the vertical direction within the container in response to changes in the rotational speed.

In the specimen disrupting apparatus of the present disclosure, it is desirable for the driving unit to comprise a support member for supporting the upper portion of the container in a state in which the container is not rotatable about the central axis of the container, a rotating member that rotates around a predetermined rotational axis, and connecting means for directly or indirectly connecting the lower portion of the container to the rotating member in a state where the central axis intersects with the rotational axis. In the specimen disrupting method of the present disclosure, it is preferable for rotation to be performed in a state where the central axis of the container intersects with the rotational axis about which the lower portion of the container rotates.

In the specimen disrupting apparatus and method of the present disclosure, it is preferable for the angle at which the central axis intersects with the rotational axis to be within a range from 2 to 5 degrees.

Further, in the specimen disrupting apparatus of the present disclosure, the support member may comprise a flexible member having a hole therein, through which the upper portion of the container is inserted.

In addition, in the specimen disrupting apparatus of the present disclosure, it is desirable for the flexible member to have an annular portion that is harder than the material of the flexible member, around the hole.

Further, in the specimen disrupting apparatus of the present disclosure, the connecting means may be provided with a concave portion or a convex portion provided at a position remote from the rotational axis in the rotating member and a concave portion or a convex portion for engaging the concave portion or the convex portion, provided directly or indirectly at the lower end of the container.

In addition, in the specimen disrupting apparatus of the present disclosure, it is preferable for the support member to further comprise a cylindrical container housing portion having an opening communicating with the hole of the flexible member and a bottom, wherein a convex portion is formed on the bottom of the container housing portion, and a projection that engages with a rib formed on the outer peripheral surface of the container to prevent rotation of the container about the central axis thereof is formed on the inner circumferential surface of the flexible member.

Further, in the specimen disrupting apparatus and the specimen disrupting method of the present disclosure, a plurality of containers may be simultaneously rotated. In the specimen disrupting apparatus and the specimen disrupting method according to the present disclosure, when a portion of the containers among the plurality of containers are being rotated, the remaining containers may be rotated at a different rotational speed from that of the other containers.

The specimen disrupting apparatus and the specimen disrupting method according to the present disclosure store a solution containing a specimen, a great number of small diameter beads, and a large diameter bead in a container, and the lower portion of the container is rotated at two or more continuously changing rotational speeds. Thereby, specimens can be efficiently disrupted in a short amount of time.

In addition, the specimen disrupting apparatus of the present disclosure is provided with a rib that causes the small diameter bead to bounce upward from the inner circumferential surface. Thereby, the small beads positioned at the upper portion of the container are bounced upward from the inner circumferential surface, and then dispersed in the solution. Accordingly, the specimens can be efficiently disrupted in a shorter amount of time.

Further, in the specimen disrupting apparatus of the present disclosure, by forming the lower portion of the inner circumferential surface of the container to be smooth so that the large diameter beads roll thereon, the rolling large diameter bead agitates the solution. Thereby, the specimens can be efficiently disrupted in a shorter amount of time.

In addition, in the specimen disrupting method of the present disclosure, the large diameter bead rolls on the inner circumferential surface of the lower portion of the container, and the small diameter beads move in the container in the vertical direction in response to changes in the rotational speed. Thereby, the small diameter beads are dispersed in the solution and the rolling large diameter beads agitates the solution. Accordingly, the specimens can be efficiently disrupted in a shorter amount of time.

DETAILED DESCRIPTION OF THE PREFERRED EMBODIMENTS

An embodiment of the present disclosure will be described in detail with reference to the attached drawings.

Figure 1:
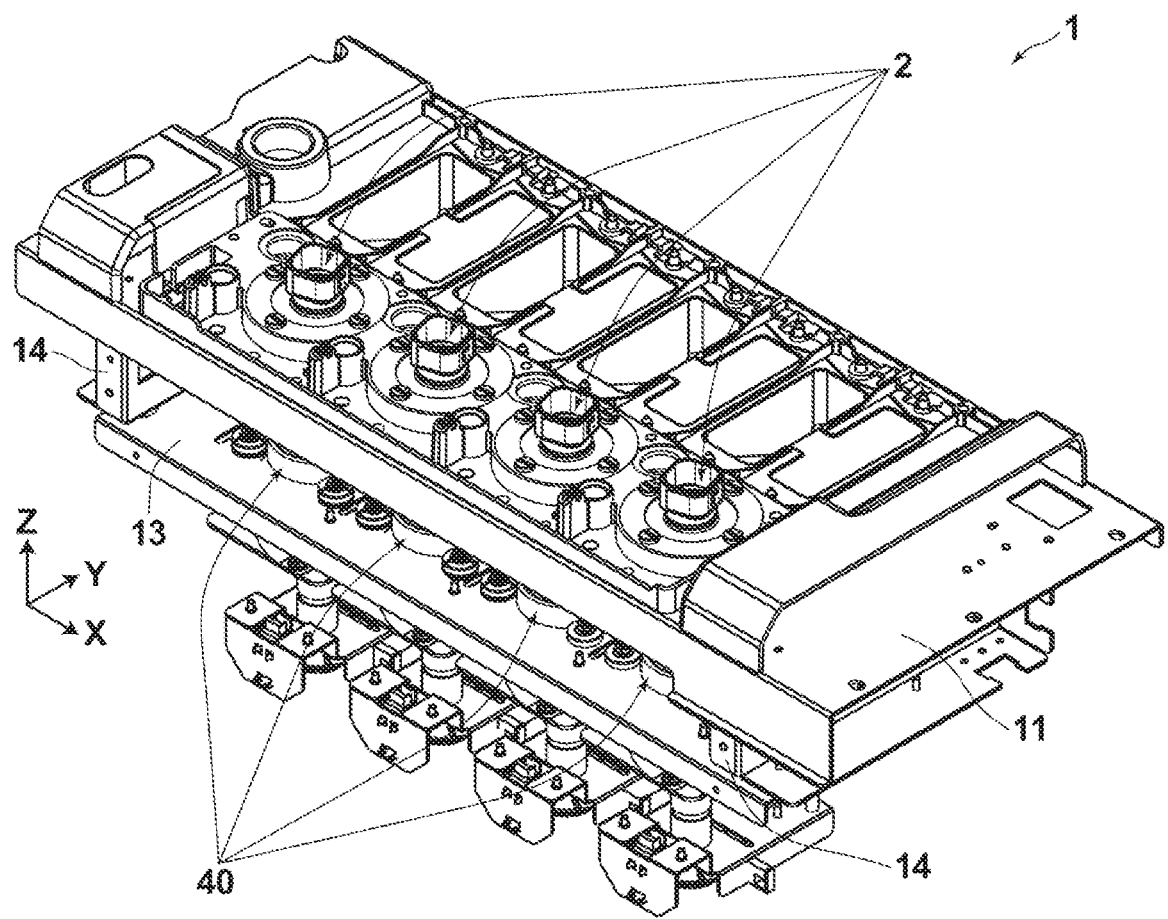
FIG. 1 is a perspective view that illustrates the overall configuration of a specimen disrupting apparatus according to an embodiment of the present disclosure.
Figure 2:
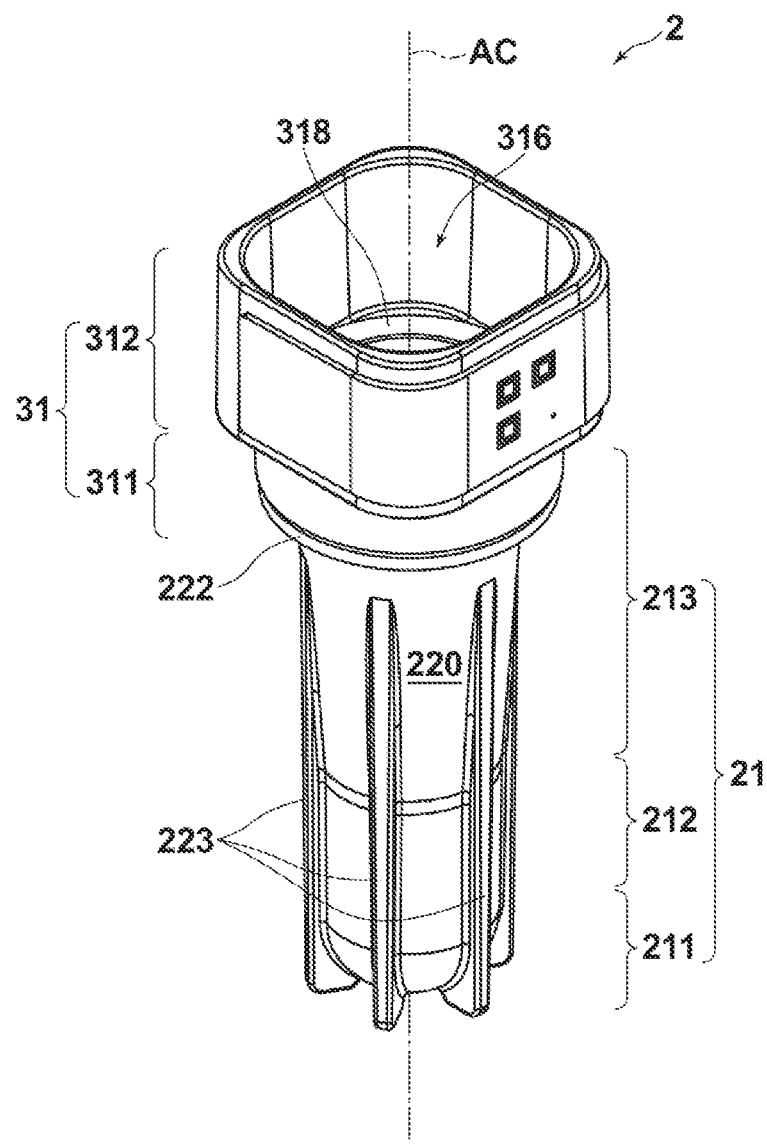
FIG. 2 is a perspective view of a container which is mounted in a specimen disrupting apparatus according to an embodiment of the present disclosure.
Figure 3:
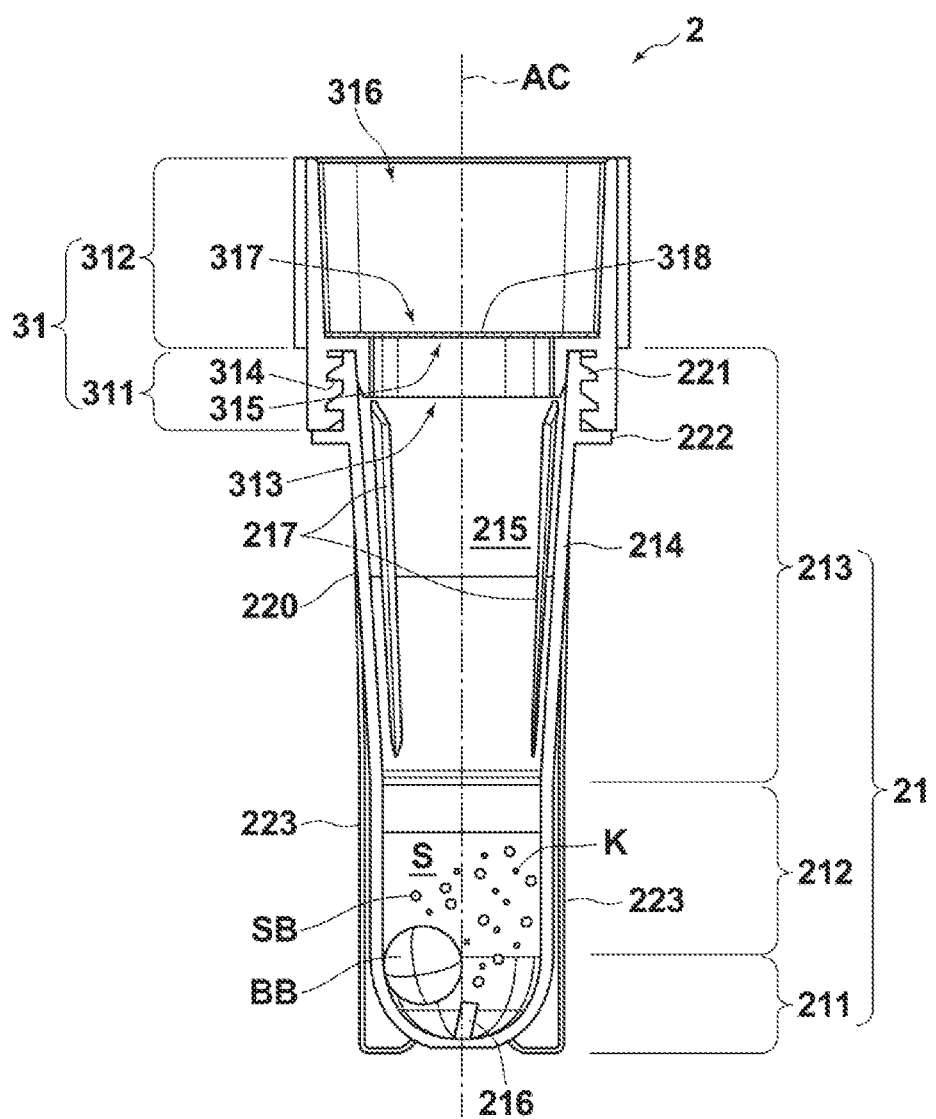
FIG. 3 is a cross sectional view of the container which is mounted to the specimen disrupting apparatus according to the embodiment of the present disclosure.

FIG. 1 illustrates the overall configuration of a specimen disrupting apparatus 1 according to one embodiment of the present disclosure. FIG. 2 is a perspective view of a container 2 which is mounted as a cartridge in the specimen disrupting apparatus 1. FIG. 3 is a sectional view of the container 2.

First, the container 2 will be described. The container 2 has stored therein a solution S containing the specimen K, a great number of small diameter beads SB, and a large diameter bead BB. A plurality of large diameter beads BB may be stored in the container 2. Further, the container 2 may store beads having diameters which are different from those of either of the large diameter beads BB and the small diameter beads SB.

The container 2 is constituted by a cylindrical body 21 and a lid body 31. The cylindrical body 21 has a substantially hemispherical bottom portion 211, a cylindrical lower portion 212 continuing from the bottom portion 211, and an upper portion 213 of a substantially inverted truncated cone shape continuous from the lower portion 212 and having a circular opening at its upper end. Note that the upper portion 213 may be of a round columnar shape.

The cylindrical body 21 will be described. In the cylindrical body 21, the height of the bottom portion 211 is about 15%, the height of the lower portion 212 is about 25%, and the height of the upper portion 213 is about 60% with respect to the height of the cylindrical body 21 in the direction of a central axis AC thereof. Note that the proportion occupied by each part in the cylindrical body 21 is not particularly limited.

The cylindrical body 21 has a substantially uniform peripheral wall 214. The inner circumferential surface 215 of the peripheral wall 214 has a concave semispherical shape having a substantially uniform radius of curvature in the vicinity of the bottom portion 211 and a circular surface having a substantially uniform diameter in the cross section orthogonal to the central axis AC in the vicinity of the lower portion 212. The vicinity of the upper portion 213 is formed in a planar shape which becomes a circle having a diameter such that the cross section orthogonal to the central axis AC expands upward.

A plurality of upwardly protruding lower ribs 216 are formed on the inner circumferential surface 215 in the vicinity of the bottom portion 211. The lower ribs 216 agitate the solution S. The lower ribs 216 are preferably formed at equal angular intervals with respect to the central axis AC, and the cross section orthogonal to the central axis AC of each of the lower ribs 216 is rectangular. In the present embodiment, three lower ribs 216 having a height of about 3 mm are formed at angular intervals of 120 degrees from each other. The height and angular interval of the lower ribs 216 can be appropriately adjusted according to the type and the content of the specimen K, and is not particularly limited. However, but it is preferable for the heights and the angular intervals of the lower ribs 216 to be those that enable the solution S to be agitated, and cause the small diameter beads SB or the large diameter bead BB rolling inside the container 2 to collide therewith during rotation to cause the trajectories thereof to be irregular.

The inner circumferential surface 215 is formed in a surface shape having no grooves, protrusions, or the like in the vicinity of the lower portion 212. A plurality of upper ribs 217 protruding in the central axis AC direction are formed on the inner circumferential surface 215 in the vicinity of the upper portion 213. The upper ribs 217 also agitate the solution S. The upper ribs 217 are formed at equal angular intervals with respect to the central axis AC.

In the present embodiment, three upper ribs 217 are formed at angular intervals of 120 degrees from each other. In addition, the upper ribs 217 extend upward from the vicinity of the boundary with the lower portion 212. The cross sectional shape of the upper ribs 217 in a direction orthogonal to the central axis AC is rectangular. Also, the top surfaces of the upper ribs 217 are substantially flush with the inner circumferential surface 215 in the vicinity of the boundary with the lower portion 212. As the upper ribs 217 extend upward, the top surfaces thereof continuously become higher. The number, the dimension of height, the angular intervals, and the cross sectional shape of the upper ribs can be changed as appropriate according to the type, the viscosity, the content, and the like of the solution, and is not particularly limited. However, but it is preferable for the heights and the angular intervals of the upper ribs 217 to be those that enable the solution S to be agitated and cause the small diameter beads SB rolling inside the container 2 to collide therewith during rotation to cause the trajectories thereof to be irregular.

Screw threads 221 to be threadedly engaged with the lid body are formed on the outer peripheral surface 220 of the upper portion 213, and an annular flange 222 is formed below the threads 221. The lid body 31 is threadedly engaged with the cylindrical body 21 up to a position at which the lower end of the lid body 31 approaches the flange 222.

A plurality of outwardly projecting outer ribs 223 are formed on the outer peripheral surface 220 below the flange 222. The outer ribs 223 are utilized to engage the container 2 with the specimen disrupting apparatus 1. The outer ribs 223 extend downward from the vicinity of the flange 222 to the lower end of the bottom portion 211. Further, the outer ribs 223 are formed at equal angular intervals with respect to the central axis AC.

In the present embodiment, six of the outer ribs 223 are formed at angular intervals of 60 degrees from each other. The cross section orthogonal to the central axis AC of each of the outer ribs 223 is rectangular. Further, the lower end of the outer rib 223 has a flat surface shape such that the container 2 is capable of maintaining an upright posture when the container 2 is placed on a flat surface. This improves workability by the user.

The top surfaces of the outer ribs 223 are substantially flush with the outer peripheral surface 220 at the upper ends of the outer ribs 223. As the outer ribs 223 extend downward, its top surfaces thereof continuously become higher. Thereby, the distances between the central axis AC and the top surfaces of the outer ribs 223 become substantially constant. The number, the dimension of height, the angular interval, and the cross sectional shape of the outer ribs 223 can be changed as appropriate according to the engaging structure of the specimen disrupting apparatus 1, and are not particularly limited.

The lid body 31 is constituted by a substantially cylindrical lower lid portion 311 and a substantially rectangular parallelepiped upper lid portion 312. The lower lid portion 311 has a substantially circular concave portion 313 formed from the lower end thereof. A screw groove 314 to threadedly engage with the screw thread 221 of the cylindrical body 21 is formed on the side peripheral surface of the concave portion 313. A circular opening 315 that communicates with the upper lid portion 312 is formed in the concave portion 313.

A concave portion 316 having a substantially square shape is formed in the upper lid portion 312 from the upper end thereof. A circular opening 317 that communicates with the opening 315 is formed in the concave portion 316. The opening 317 is sealed with a metal film 318. The metal film 318 has a thickness to a degree that it can be pierced with an extraction needle etc. after the disrupting process. Note that the material of the metal film is aluminum or stainless steel, but it is not particularly limited. In addition, the metal film alternatively may be a resin film. The material of the resin film is polypropylene, polyethylene or the like, but is not particularly limited.

By the configurations described above, it is unnecessary to release the threaded engagement between the cylindrical main body 21 and the lid body 31 in order to collect the solution S for disruption treatment, and workability is improved. Furthermore, it is possible to reduce the occurrence of contamination by releasing the threaded engagement.

The specimen disrupting apparatus 1 will be described. The container 2 is mounted as a cartridge in the specimen disrupting apparatus 1. The specimen disrupting apparatus 1 is an apparatus for disrupting a specimen in the solution S. The specimen disrupting apparatus 1 comprises a support frame 11 for supporting the upper portions of a plurality of containers 2, a plurality of drive units 40 for rotating the lower portions of the plurality of containers 2, a fixing frame 13, and a connecting frame 14 that connects the support frame 11 and the fixing frame 13.

The support frame 11 supports four containers 2 arranged in the direction of the X axis in FIG. 1 with predetermined intervals therebetween. The containers 2 are mounted in an orientation in which it is substantially upright in the Z-axis direction in FIG. 1. The number of the containers 2 to be mounted, the arrangement direction, and the interval are not particularly limited. The fixing frame 13 fixes the four drive units 40 such that the four drive units 40 are located underneath the containers 2.

Figure 4:
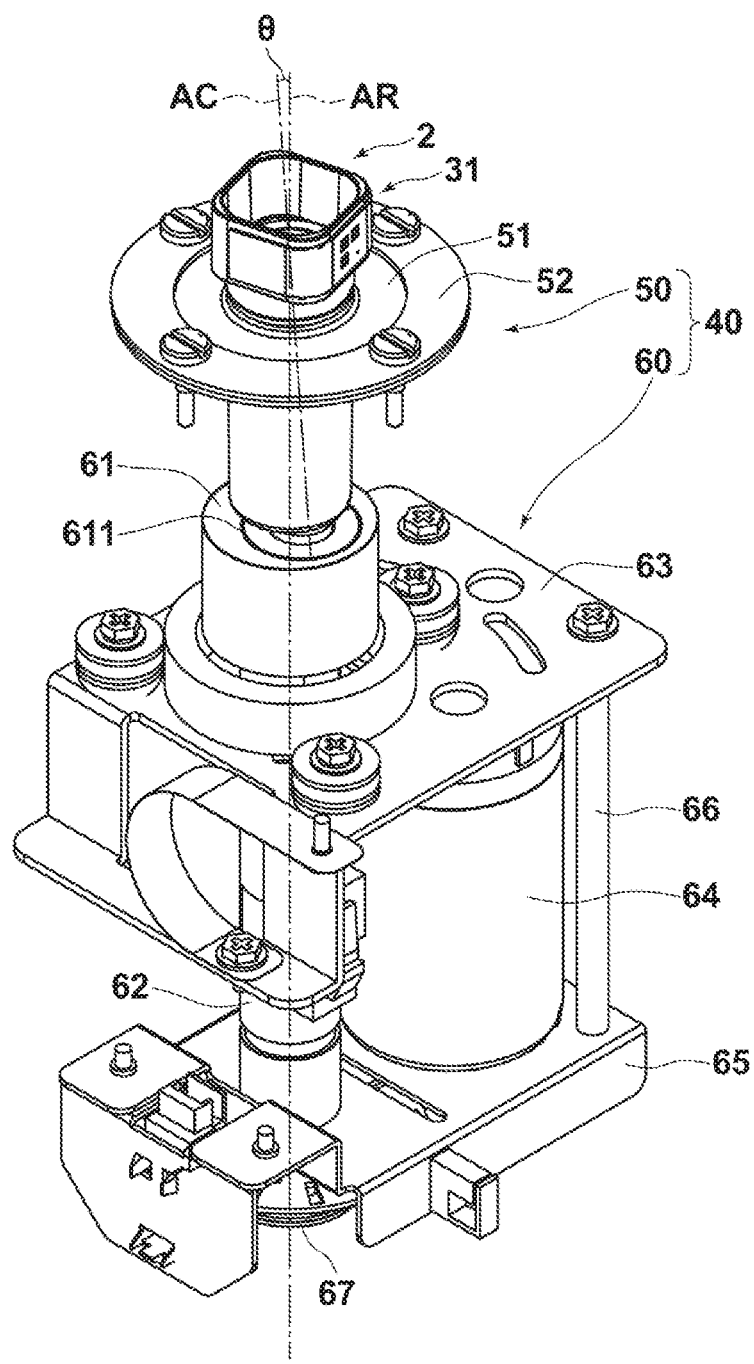
FIG. 4 is a perspective view of a drive unit of the specimen disrupting apparatus according to the embodiment of the present disclosure.

FIG. 4 is a perspective view of the drive unit 40. The drive unit 40 includes a housing unit 50 for housing the container 2 and an eccentric rotation unit 60 connected to the housing unit 50 to cause the housing unit 50 to rotate eccentrically.

The housing unit 50 is constituted by a housing/rotating member 51 that houses and rotates the container 2 in a state where the lid body 31 is exposed, and a metal ring 52 that clamps the housing/rotating member 51 between the housing/rotating member 51 and the support frame 11. The housing/rotating member 51 is connected to the eccentric rotation unit 60 at the lower end thereof. Further, screw mounting holes (not shown) are formed in the metal ring 52.

The eccentric rotation unit 60 includes a rotary plate 61 connected to the housing/rotating member 51, a rotary shaft 62 for transmitting rotary motion to the rotary plate 61, an upper bracket 63 that rotatably holds the distal end portion of the rotary shaft and fixes the rotation unit 60 to the fixing frame 13, a motor 64 that rotates the rotary shaft 62, a lower bracket 65 that rotatably holds the base end portion of the rotary shaft 62 and fixes the motor 64, and a post 66 that connects the upper bracket and the lower bracket 65.

The eccentric rotation unit 60 includes a drive pulley (not shown) attached to the drive shaft of the motor 64, a driven pulley (not shown) attached to the base end portion of the rotary shaft 62, and a belt 67 wound about the pulleys in order to transmit rotational motion of the motor 64 to the rotary shaft 62.

A circular hole 611 is formed in the rotary plate 61. The hole 611 is used for connecting with the housing/rotating member 51. The hole 611 is opened at a position offset from the rotational axis AR by a predetermined distance. The center of the rotary plate 61 is on the rotational axis AR.

Figure 5:
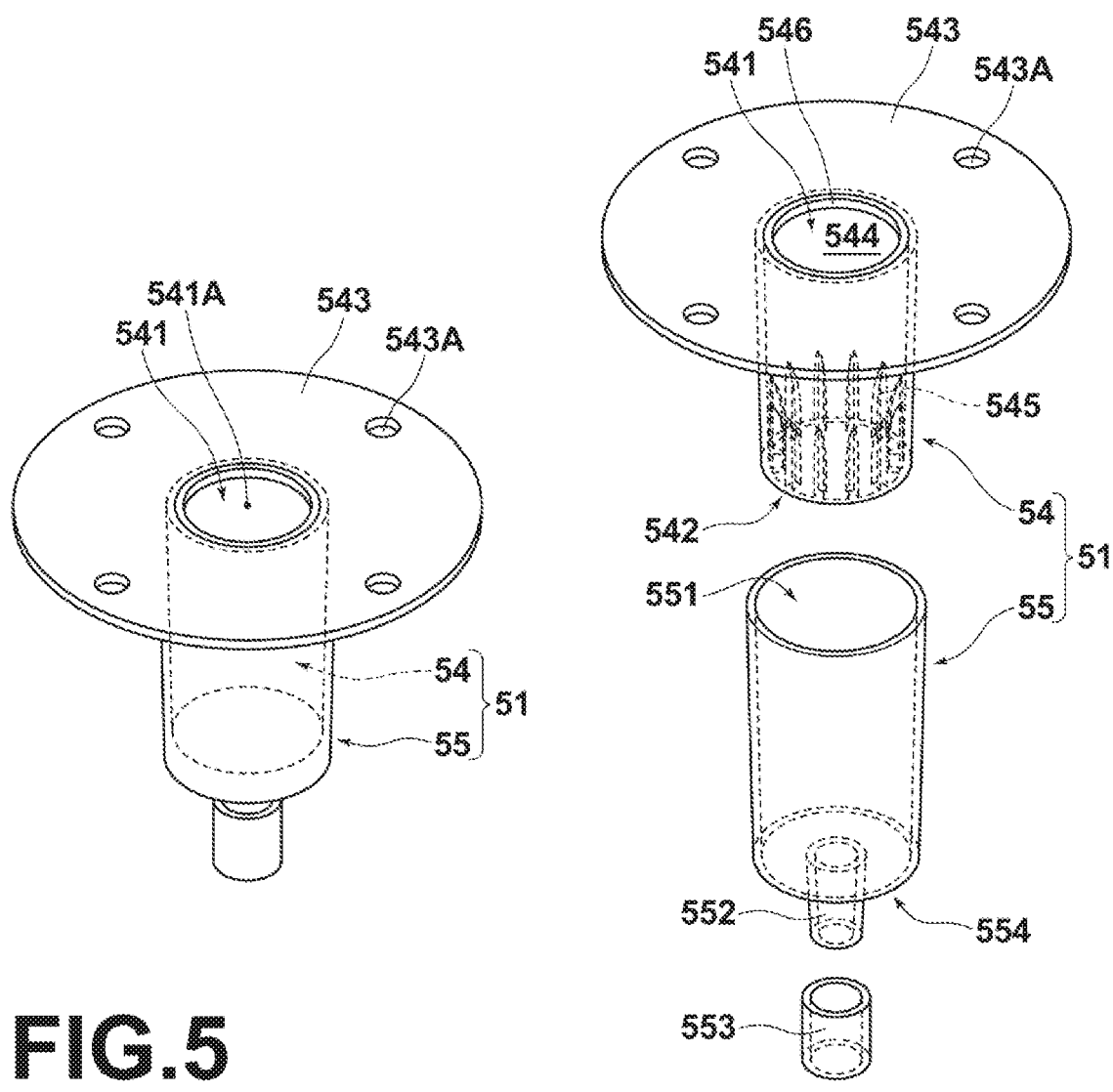
FIG. 5 is an overall view and exploded view of a housing unit of a specimen disrupting apparatus of the present disclosure.

The housing/rotating member 51 will be described. FIG. 5 is a diagram that illustrates the entire configuration and a disassembled state of the housing/rotating member 51. The housing/rotating member 51 is constituted by a container supporting portion 54 having flexibility, and a connecting tube 55. The container supporting portion 54 is covered by the connecting tube 55. The container supporting portion 54 and the connecting tube 55 are fixed to each other. The container supporting portion 54 is formed by polyurethane, and the connecting tube 55 is formed by integrally molded polypropylene. The material of the container supporting portion 54 is not particularly limited as long as it has flexibility. The material of the connecting tube 55 is also not particularly limited.

The container support portion 54 is of a bottomless cylindrical shape having a circular opening 541 at the upper end and a circular opening 542 at the lower end, and a flange 543 is formed at the upper end. Four mounting holes 543A corresponding to the mounting holes of the metal ring 52 are formed in the flange 543. The housing unit 50 and the eccentric rotation unit 60 are connected such that the center 541A of the opening 541 is positioned on the rotational axis AR.

The connecting tube 55 is of a bottomed cylindrical shape having an opening 551 at the upper end and a bottom 554 at the lower end. The container support portion 54 is inserted through the opening 551. A downwardly projecting protrusion 552 is formed at the bottom 554. The protrusion 552 is fitted into the hole 611 of the rotary plate 61 and is used to connect the connecting tube 55 and the rotary plate 61. The protrusion 552 may be inserted directly into the hole 611, or may be inserted indirectly via a resin tube 553, for example. It is also possible to form a hole of a size to a degree that the container 2 will not fall onto the bottom 554 and to form an upwardly projecting protrusion on the rotary plate 61 to establish the connection.

Figure 6:
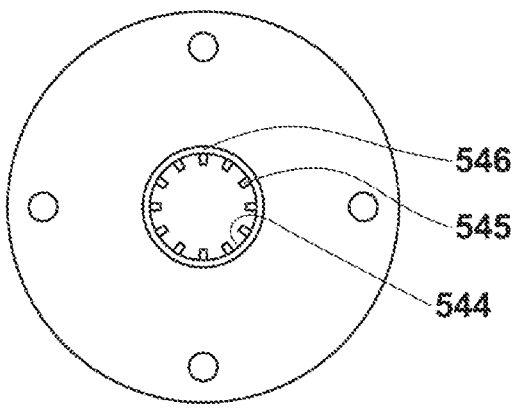
FIG. 6 is a structural view of the interior of a flexible member of the specimen disrupting apparatus of the present disclosure.

FIG. 6 is a diagram that illustrates the interior structure of the container support portion 54. A plurality of engaging ribs 545 protruding toward the central axis direction of the container supporting portion 54 are formed on the inner circumferential surface 544 of the container supporting portion 54. The engagement ribs 545 engage the container 2 with the container support portion 54 by inserting the outer ribs 223 of the cylindrical body 21 through the grooves among the engagement ribs 545. Thereby, it is possible to prevent the container 2 from rotating with respect to the container support portion 54.

In the present embodiment, twelve engaging ribs 545 having heights of approximately 3 mm are formed at angular intervals of 30 degrees from each other. The number, height and angular interval of the engaging ribs 545 can be changed as appropriate according to the structure of the outer ribs 223.

A reinforcing ring 546 is fitted within the inner circumferential surface 544 in the vicinity of the upper end of the container supporting portion 54. The reinforcing ring 546 prevents portions in contact from becoming worn due to direct contact between the container 2 and the container supporting portion 54 during operation. The material of the reinforcing ring 546 is not particularly limited as long as it is harder than the container supporting portion 54, but a metal material such as aluminum or stainless steel is preferable.

The container 2 is inserted through the opening 541 while the outer ribs 223 and the engaging ribs 545 are engaged, abuts the bottom 554, and is received. In addition, rotation of the container 2 relative to the housing unit 50 is prevented by the engagement between the outer ribs 223 and the engagement ribs 545. Further, the container 2 is housed in a state in which the center 541A thereof is on the substantially central axis AC of the container 2.

As described above, the center 541A of the container support portion 54 is positioned on the substantially rotational axis AR, and the protrusion 552 is connected to the hole 611, which is offset from the rotational axis AR. Therefore, the housed container 2 rotates in a state in which the central axis AC and the rotational axis AR intersect. During rotation, the minute rotation of the upper portion of the container 2 is absorbed by the flexibility of the container support portion 54.

In the present embodiment, the distance from the center 541A to the bottom 554 occupies about 70% of the length in the direction of the central axis AC of the container 2. The angle θ between the central axis AC of the container 2 and the rotational axis AR of the rotary plate 61 is preferably within a range from 2 to 5 degrees.

Figure 7:
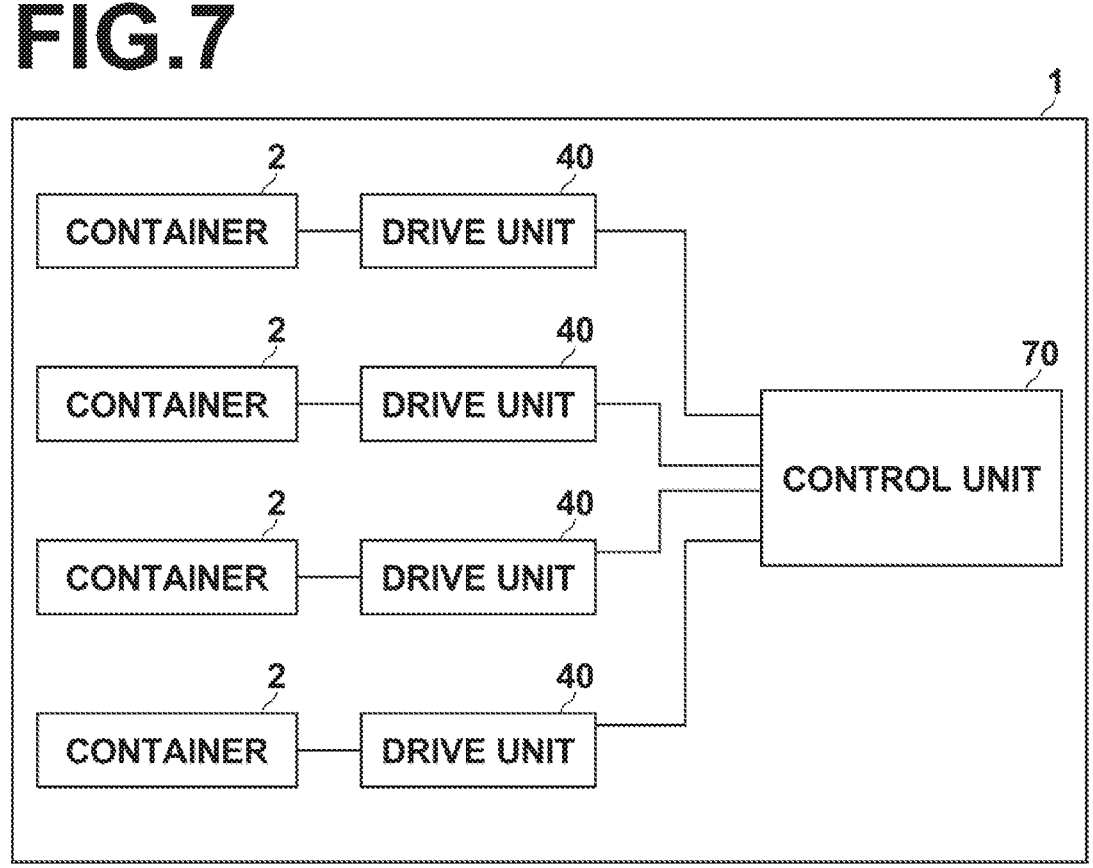
FIG. 7 is a block diagram that illustrates a control system of the specimen disrupting apparatus of the present disclosure.

Next, a control system of the specimen disrupting apparatus 1 will be described. FIG. 7 is a block diagram that illustrates the control system of the specimen disrupting apparatus 1. In the specimen disrupting apparatus 1, the four driving units 40 are independently controlled by one control unit 70. The control unit 70 controls the driving units 40 such that the four driving units 40 rotate the lower portions of the containers 2 simultaneously.

In addition, the control unit 70 controls the driving units 40 such that the rotational speeds of the lower portions of the containers 2 repeatedly change between a low rotational speed and a high rotational speed. Specifically, the control unit 70 controls the motor 64 by a PWM (Pulse Width Modulation) method such that the rotational speed of the rotary plate 61 continuously changes between the low rotational speed and the high rotational speed. In this case, it is preferable for control to be exerted such that there is no time during which rotation does not occur between the low rotational speed and the high rotational speed. In the present embodiment, the motor 64 is a direct current motor, but the type of motor is not particularly limited.

It is desirable for the low rotational speed to be within a range of 1000 rpm to 5000 rpm, and more preferably within a range of 1000 rpm to 4000 rpm. It is desirable for the high rotational speed to be within a range from 6000 rpm to 10000 rpm, more desirably within a range from 6000 rpm to 9000 rpm, even more preferably within a range from 7000 rpm to 9000 rpm, and most preferably within a range from 7000 rpm to 8000 rpm. In addition, it is desirable for the high rotational speed and the low rotational speed to be in the ranges above, and for the difference in rotational speeds to be within a range from 1000 rpm to 9000 rpm, more desirably within a range from 2000 rpm to 8000 rpm, even more desirably within a range from 3000 rpm to 7000 rpm, and most desirably within a range from 4000 rpm to 7000 rpm.

In addition to the low rotational speed and the high rotational speed, the control unit 70 may exert control so as to repeat rotation among three or more types of rotational speeds including a medium rotational speed, for example.

Figure 8:
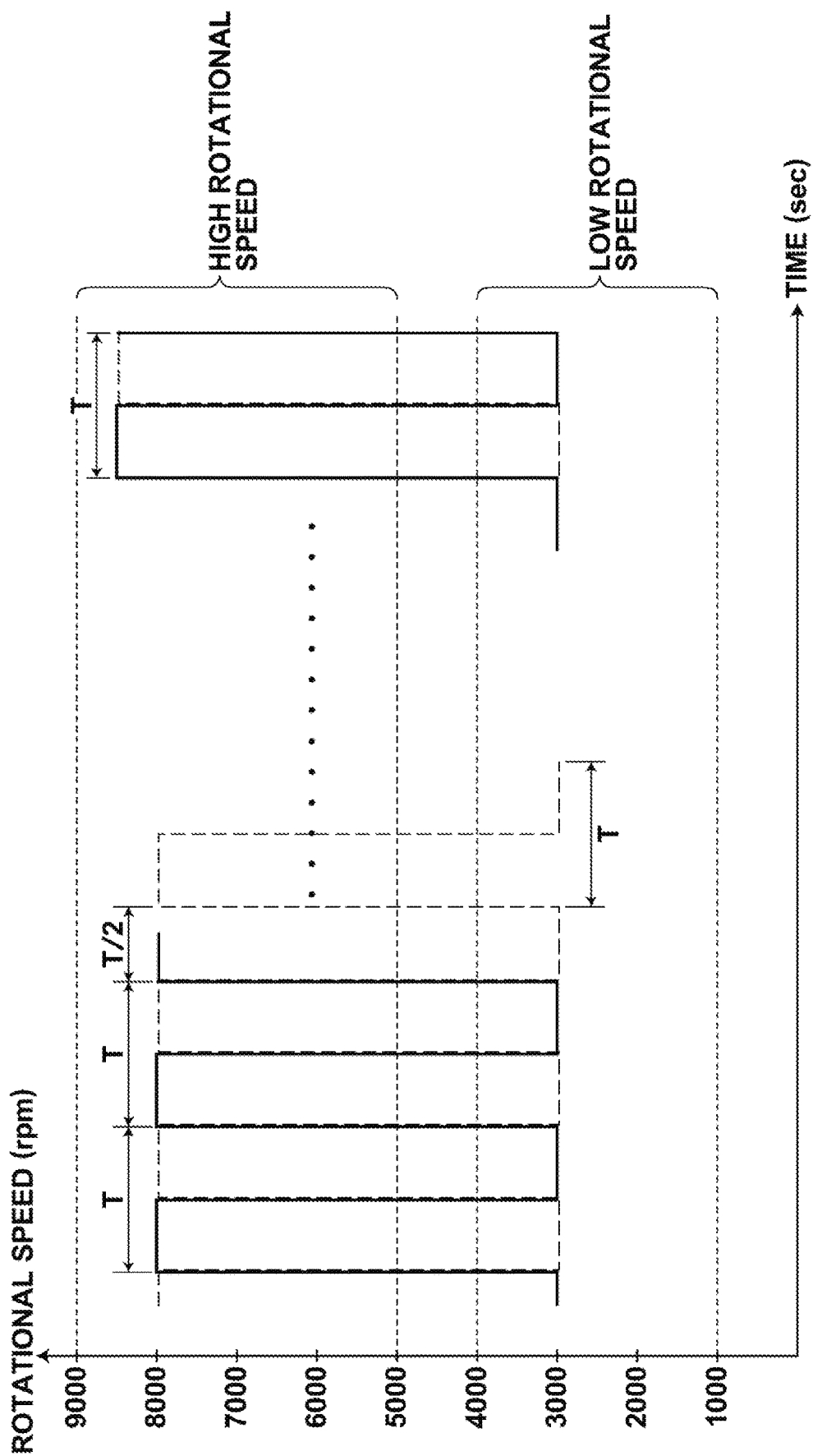
FIG. 8 is a diagram that illustrates changes in the rotational speed of a container imparted by the specimen disrupting apparatus of the present disclosure.

FIG. 8 is a diagram illustrating changes in the number of revolutions with respect to a temporal axis. As indicated by the solid line in FIG. 8, the control unit 70 controls the driving unit 40 such that the rotational speed changes between the low rotational speed and the high rotational speed at a substantially constant cycle T by a predetermined number of repetitions. In the present embodiment, the control unit 70 controls the driving unit 40 so that the waveform indicating the change in the rotational speed becomes a substantially rectangular wave. The waveform indicating the change in the number of rotations is not particularly limited. For example, it may be a sine wave, a triangular wave, or the like, and the waveform at the low rotational speed and the waveform at the high rotational speed may be different. Note that the waveform need not be an exact rectangle but may be a waveform approximating a rectangle which includes a delay with respect to a control command from the control unit 70, due to mechanical backlash or the like of the driving units 40. In FIG. 8, as an example, the low rotational speed is set to 3000 rpm and the high rotational speed is set to 8000 rpm in all of the cycles T. Alternatively, the low rotational speed may be set within a range from 1000 rpm to 5000 rpm, and/or high rotational speed may be set to different values within a range from 6000 rpm to 10000 rpm. The rotational speeds may be set differently for each cycle, or set differently for at least one period.

The cycle T and the number of repetitions are adjusted as appropriate according to the type of specimen, the amount of the stored solution, etc. However, it is preferable for the cycle T to be within a range from 3 to 10 seconds, for the number of repetitions to be within a range from 4 to 30, and more preferably within a range of 10 to 20 times. Also, the control unit 70 may divide the four driving units 40 into two groups, and while the driving units 40 belonging to one group causes the lower portions of the containers rotate at a high rotational speed, the driving units belonging to the other group 40 may be controlled to cause rotation at a low rotational speed.

In the present embodiment, while the control unit 70 controls the two driving units 40 to cause the two containers 2 to rotate along the waveform indicated by the solid line in FIG. 8, the other two driving units 40 rotate the two containers 2 along the waveform of the broken line, the phase of which differs from the solid line different by half of a cycle T/2. This enables reduction of resonance caused by rotation of all the drive units 40 at the same rotational speed.

Figure 9:
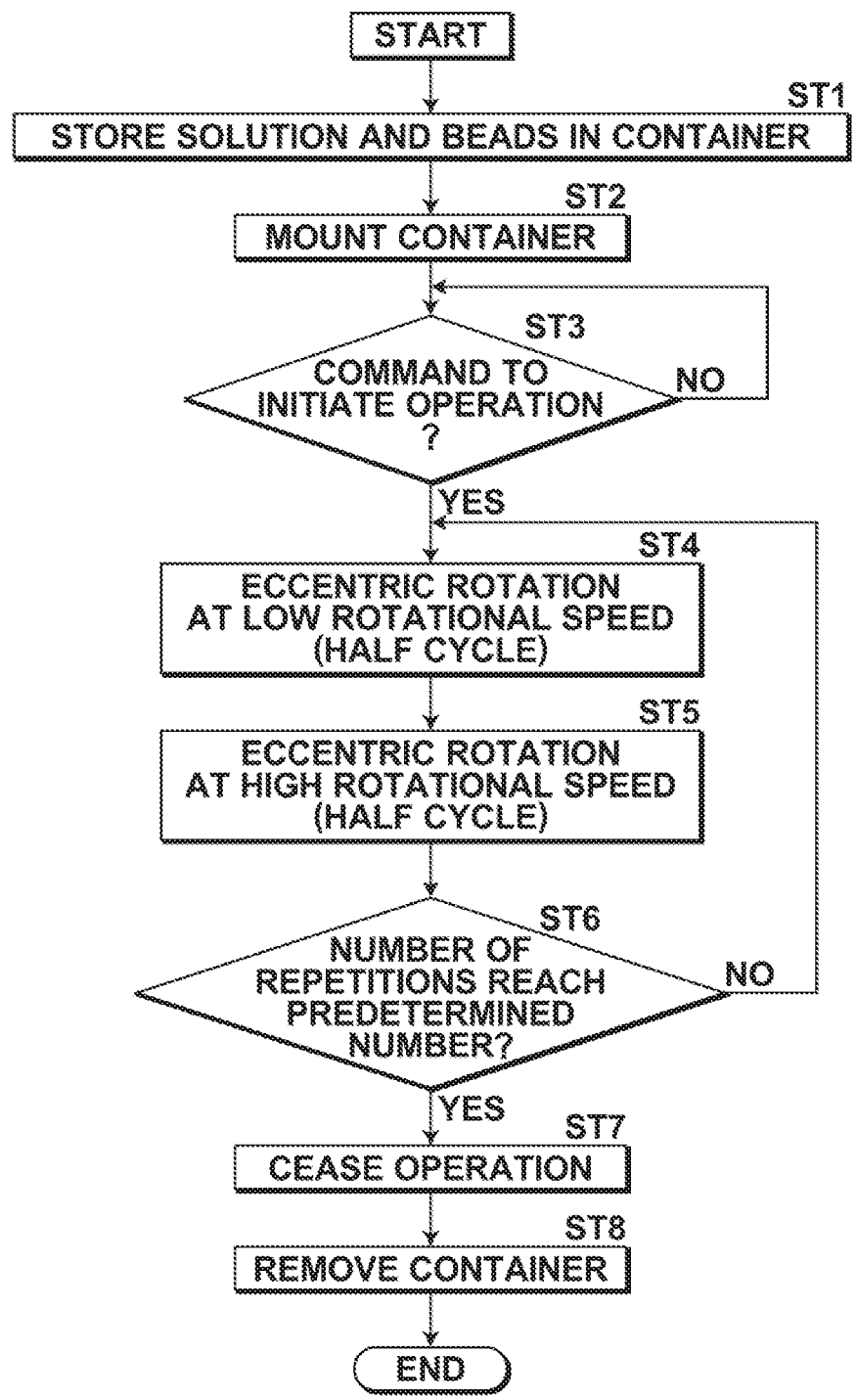
FIG. 9 is a flowchart that illustrates the steps of a disrupting method which is executed by the specimen disrupting apparatus of the present disclosure.

Next, a method of disrupting a specimen by the specimen disrupting apparatus 1 will be described with reference to the flowchart of FIG. 9. First, the solution S, a large diameter bead BB, and many small diameter beads SB are stored in the cylindrical body 21 (ST 1). The lid body 31 and the cylindrical body 21 are threadedly engaged with each other to mount the container 2 (ST 2).

A signal from a sensor for confirming a user command or mounting of the container 2 is received (ST 3), and the container 2 is eccentrically rotated for a half cycle T/2 at a low rotational speed (ST 4). Next, eccentric rotation is performed for a half cycle T/2 at a high rotational speed (ST 5). Note that (ST 4) may be eccentric rotation at a high rotational speed, and (ST 5) may be eccentric rotation at a low rotational speed.

Whether the number of repetitions of the cycle T has reached a number received from the user or a preset number is checked (ST 6), and if not, the process returns to step (ST 4) again. If the number of repetitions of the cycle T has reached the number received from the user or the preset number, the operation of the specimen disrupting apparatus 1 is ceased (ST 7). The container 2 is removed from the specimen disrupting apparatus 1 (ST 8), the solution S is extracted, and the process is completed.

Next, the specimen K will be described. The specimen K is not particularly limited as long as there is a possibility that it contains bacterial bodies and viruses. Specifically, bodily fluids (blood, serum, plasma, cerebrospinal fluid, tears, sweat, urine, pus, nasal mucous, sputum, etc.), excreta (feces, etc.), organs, tissues, skin, pressed specimens (swabs) considered to include such matter, gargling liquid, culture liquid, etc. of animals (particularly humans) may be employed as the specimen K.

Examples of the above bacterial cells and viruses include bacteria such as *Mycobacterium tuberculosis, Streptococcus pneumoniae*, diphtheriae, *Neisseria meningitidis, Neisseria gonorrhoeae*, staphylococcus, streptococcus, enterobacteria, *Escherichia coli*, and *Helicobacter pylori*, etc., viruses such as rubella virus, herpes virus, hepatitis virus, ATL virus, AIDS virus, influenza virus, adenovirus, enterovirus, poliovirus, EB virus, HAV, HBV, HCV, HIV, HTLV, etc., and fungi such as candida, cryptococcus, etc.

The specimen K may be employed as is. However, in the present embodiment it is employed as the solution S diluted with an appropriate diluent. Note that the diluent may have bactericidal properties if necessary, and may contain a digestive enzyme or a denaturing agent.

Examples of the aforementioned diluent include water, a buffer solution, etc., which are generally used in this field. Examples of the buffer solution include a tris hydroxyl aminomethane buffer solution, a phosphate buffer solution, a boric acid buffer solution, and a Good's buffer solution. The concentration of the buffer is generally within a range from 5 mM to 500 mM, and preferably within a range from 20 mM to 200 mM.

Next, each bead will be described. The material of the large diameter beads BB and the small diameter beads SB is not particularly limited as long as it has a hardness capable of imparting physical impact to the specimen. However, beads made of glass, garnet and/or zirconia are desirable, and among these, zirconia beads are more desirable.

The shape of the small diameter beads SB is also not particularly limited as long as it is easily dispersed in the solution S. The shape of the large diameter bead BB is not particularly limited as long as the shape facilitates rolling on the inner circumferential surface 215 of the container 2. Note that it is desirable for both the small diameter beads SB and the large diameter bead BB to be of spherical shapes.

The diameters of the small diameter beads SB are preferably within a range from approximately 0.1 mm to 1 mm. The diameter of the large diameter bead BB is preferably greater than the diameters of the small diameter beads SB by a factor of several 10's. Specifically, the diameter of the large diameter bead BB is within a range from 1 to 10 mm, and preferably within a range from 3 to 8 mm.

Figure 10:
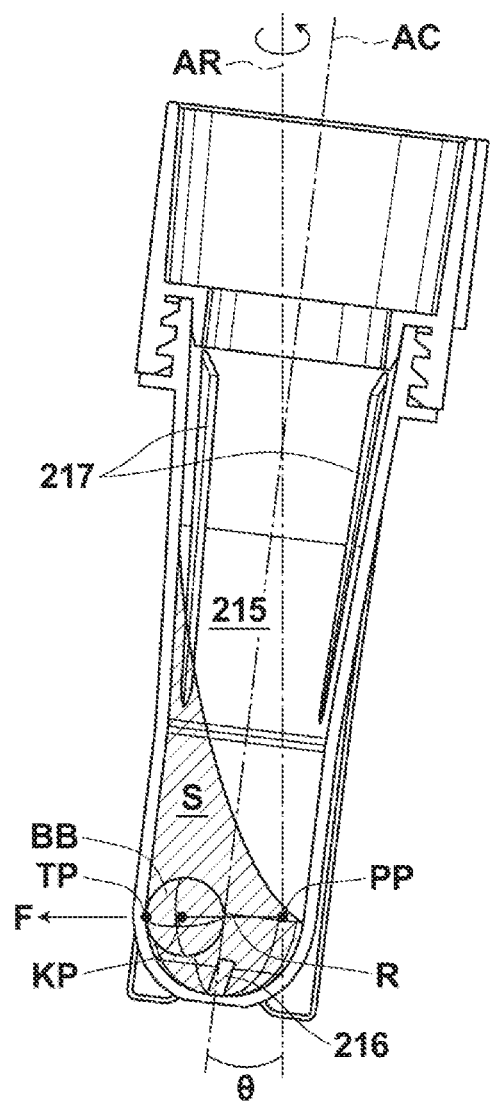
FIG. 10 is a diagram that illustrates the action of a large diameter bead in the specimen disrupting apparatus of the present disclosure.

Next, the operations of the large diameter bead BB, the small diameter bead SB, the lower ribs 216, and the upper ribs 217 will be described. FIG. 10 is a diagram for explaining the operation of the large diameter bead BB during rotation. The small diameter beads SB are omitted from FIG. 10, in order to facilitate understanding.

As illustrated in FIG. 10, centrifugal force F, indicated by the arrow in the drawing, acts on the large diameter bead BB during rotation. Due to the centrifugal force F, the large diameter bead BB moves to a lower position farthest away from the rotational axis AR.

In FIG. 10, a contact point TP indicates a point where the large diameter bead BB and the inner circumferential surface 215 contact each other, and a center KP indicates the center of the large diameter bead BB. Further, a projection point PP indicates a point of the center KP projected onto the rotational axis AR. The line segment connecting the center KP and the projection point PP becomes a radius of rotation R of the large diameter bead BB.

It is desirable for the radius of rotation R to be within a range from about 8 to 12 mm. Further, under the conditions that the radius of rotation R is 8 mm, the density of the large diameter bead BB made of zirconia is 5.68 g/cm$^3$, the diameter of the large diameter bead BB is 5 mm, the low rotational speed is 3000 rpm, and the high rotational speed is 8000 rpm, the centrifugal force F is about 0.29 N at the low rotational speed and about 2.09 N at the high rotational speed, for example.

As described above, the inner circumferential surface 215 in the vicinity of the contact point TP is a flat surface without ribs, grooves, etc. Therefore, the large diameter bead BB rolls on the inner circumferential surface 215 while drawing the trajectory of a substantially constant radius of rotation R during eccentric rotation. The position of the contact point TP may be adjusted as appropriate depending on the shape of the inner circumferential surface 215.

During eccentric rotation, the solution S is agitated by the lower ribs 216 and also agitated by the rolling large diameter bead BB. The solution S which reaches the upper ribs 217 is also agitated by the upper ribs 217.

Figure 11:
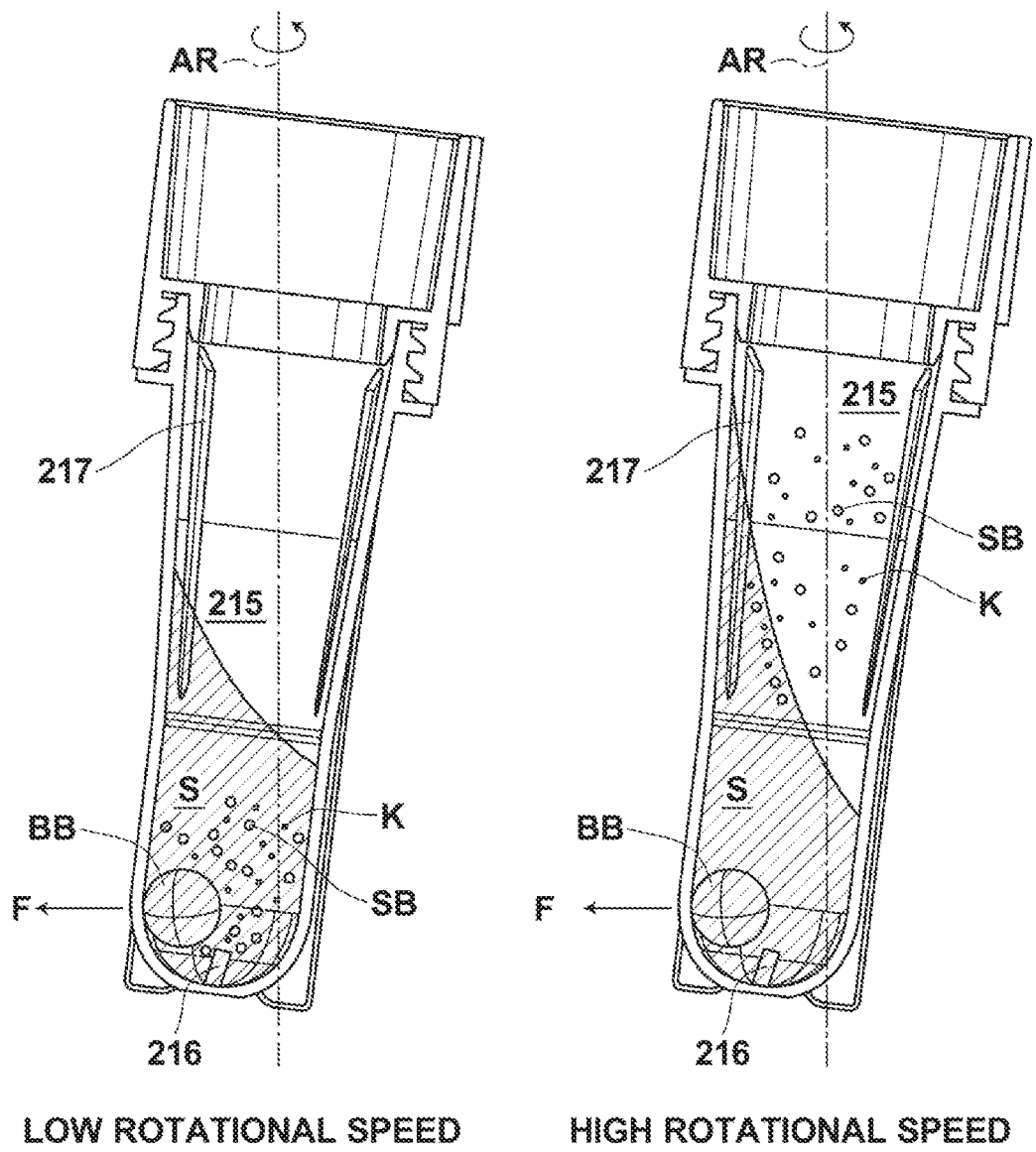
FIG. 11 is a diagram that illustrates the manner of agitation by the specimen disrupting apparatus of the present disclosure.

FIG. 11 illustrates the manner in which the solution S is agitated during low speed rotation. The drawing on the left of FIG. 11 illustrates the manner of agitation during low speed rotation and the drawing on the right of FIG. 11 illustrates the manner of agitation during high speed rotation. A vortex is generated on the liquid surface of the solution S due to stirring by the large diameter bead BB, the lower ribs 216, and the upper ribs 217.

During low speed rotation, a great number of small diameter beads SB gathers at positions at the lower portion due to the action of the centrifugal force F of the container 2, and physical impact is imparted to the specimen K due to collisions between the rolling large diameter beads BB and the small diameter beads SB as well as collisions between these beads and the inner circumferential surface 215.

When rotation changes from low speed rotation to high speed rotation, the size of the vortex within the solution S increases, and the liquid surface also rises along the inner circumferential surface 215. Therefore, the light small diameter beads SB also begin to move upward together with the solution S. Collisions occur between the small diameter beads SB that begin moving upward and the large diameter bead BB, and the physical impact applied to the specimen K increases. When the small diameter beads SB move further upward, the small diameter beads SB are bounced up from the inner circumferential surface 215 by the upper ribs 217, and are dispersed into the solution S.

When rotation returns from high speed rotation to low speed rotation, the small diameter beads SB which are dispersed in the solution S begin to move downward again. Collisions occur between the small diameter beads SB that begin moving downward and the large diameter bead BB, and the physical impact applied to the specimen K increases. As described above, by repeating the low speed rotation and the high speed rotation, thereby moving the small diameter beads SB up and down within the container 2, the frequency of collisions between the small diameter beads SB and the large diameter bead BB increases, and physical impact can be imparted efficiently to the specimen K.

In the specimen disrupting method using the disrupting apparatus of the present disclosure, the solution containing a specimen, the great number of small diameter beads SB, and a large diameter bead BB are placed in the container 2 of the present disclosure, and the container 2 is rotated while continuously changing the rotational speed among two or more different rotational speeds. Specifically, a solution containing 100 uL to 1000 uL of a sample, 5000 to 10000 small beads SB having diameters within a range from 0.1 mm to 1 mm, and a large diameter bead BB having a diameter within a range from 1 mm to 10 mm are placed in a container. A combination of rotation at a low rotational speed within a range from 1000 rpm to 5000 rpm is conducted for 3 to 10 seconds and rotation at a high rotational speed within a range from 6000 rpm to 10000 rpm is conducted for 3 to 10 seconds as one cycle, and the cycle is repeated 10 to 20 times, for example.

As described above, according to the present embodiment, the solution S containing the specimen K, the great number of small diameter beads SB, and the large diameter bead BB are stored in the container 2, and the lower portion of the container 2 is rotated while continuously changing the rotational speed among different rotational speeds. Thereby, it is possible to efficiently disrupt the specimen K in a short amount of time by increasing the collision frequency between the great number of small diameter beads SB and the large diameter bead BB.

In addition, according to the present embodiment, the upper ribs 217 bounce the small diameter beads SB up from the inner circumferential surface 215 and disperse the small diameter bead SB into the solution S. Thereby, the frequency of collision with the rolling large diameter bead BB can be increased.

In addition, according to the present embodiment, since the inner circumferential surface 215 at the lower portion of the container 2 is smooth, the large diameter bead BB is capable of rolling while drawing a constant trajectory with the radius of rotation R, and the frequency of collision with the small diameter beads SB can be increased.

In addition, according to the present embodiment, since the small diameter beads SB are moved in the vertical direction within container 2 by changing the rotational speed between low speed rotation and high speed rotation, the frequency of collision with the large diameter bead BB can be increased.

In addition, according to the present embodiment, since the four driving units 40 simultaneously rotate the lower portions of the four containers 2, a large amount of the specimen K can be disrupted efficiently at once. Further, while the two driving units 40 of the four driving units 40 rotate the lower portion of the container 2 at a low rotational speed, the other two driving units 40 rotate the lower portion of the container 2 at a high rotational speed, so that it is possible to reduce vibration which is generated in the specimen disrupting apparatus 1.

Example 1

In the examples shown below, a "*Bacillus* genus bacteria" such as "*Bacillus subtilis*" that forms "spores" was employed as the specimen K. *Bacillus* spores (5×10$^3$ ctu) are added to 600 uL of a solution S (containing sterilizing solution). One zirconia bead having a diameter of 5 mm as the large diameter beads BB and 0.4 g (about 8000) of zirconia beads having a diameter of 0.2 mm as the small diameter beads SB were placed in the container 2.

To evaluate disruption, the *Bacillus* spores (5×10$^3$ ctu) were disrupted by the specimen disrupting apparatus 1, and nucleic acids were recovered after purification. Next, the number of spores was counted under a microscope at a magnification of 400× using a bacteria calculation board (manufactured by SLGC). Spore numbers were calculated by diluting the number of cells per each square of the calculation board to 5.8, 1.0, 0.4, and 0.1.

A calibration curve was serial dilution (0 to 1×10 6/reaction) of the *B. subtilis* spore genome using distilled water. A reaction reagent composition for qPCR Syber Premix ExTaq II (10 μL), 100 nM of Bs-spo-F4-1/R4-1 (amplicon=235 bp), and a temperature cycle was started from an initial state of 95° C. (30 sec), and 45 cycles of temperatures of 95° C. (6 sec), 62° C. (20 sec), and 72° C. (20 sec) were repeated.

Figure 12:
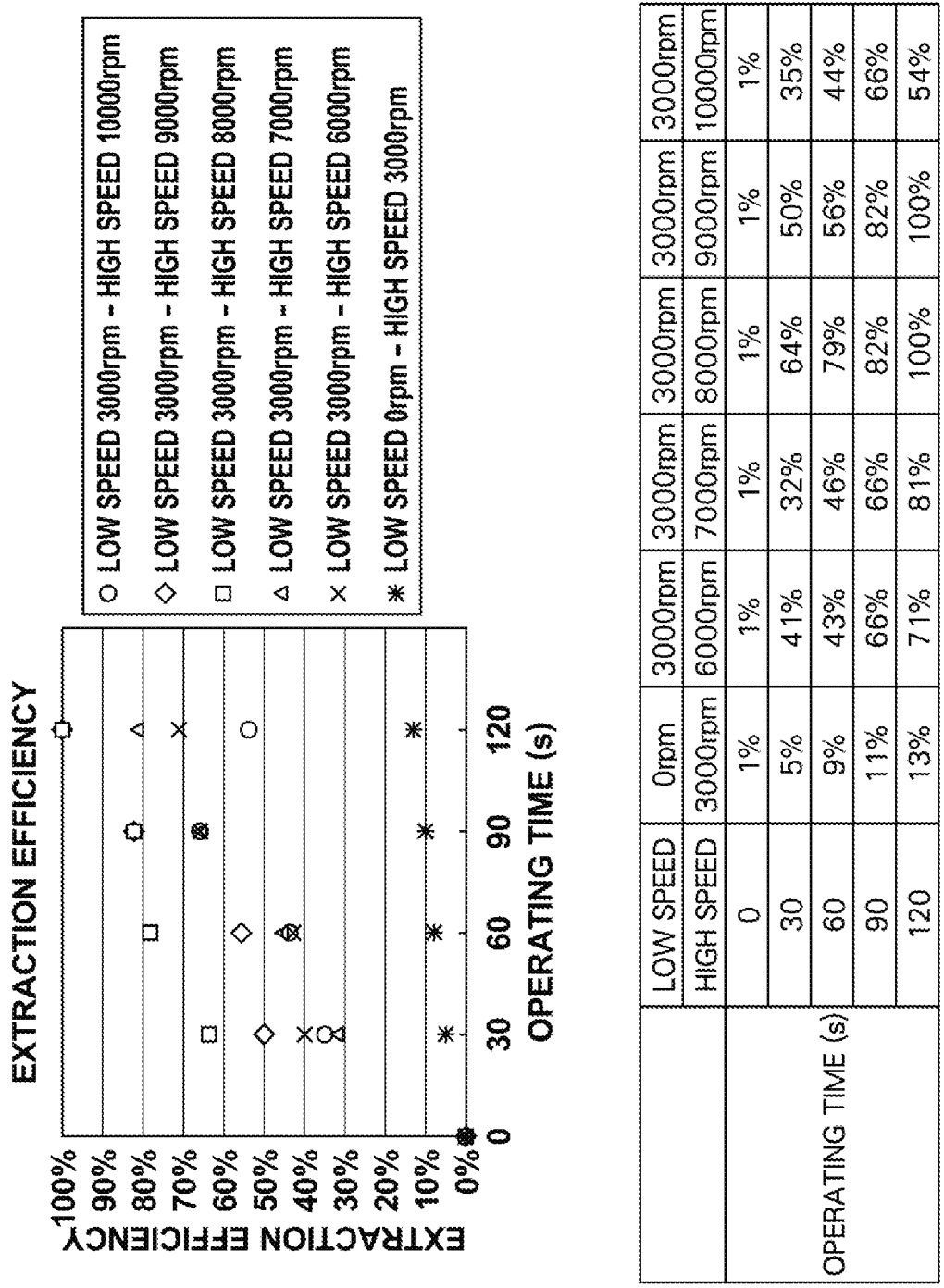
FIG. 12 is a data diagram that illustrates disruption results of a specimen by the specimen disrupting apparatus of the present disclosure (part 1).
Figure 13:
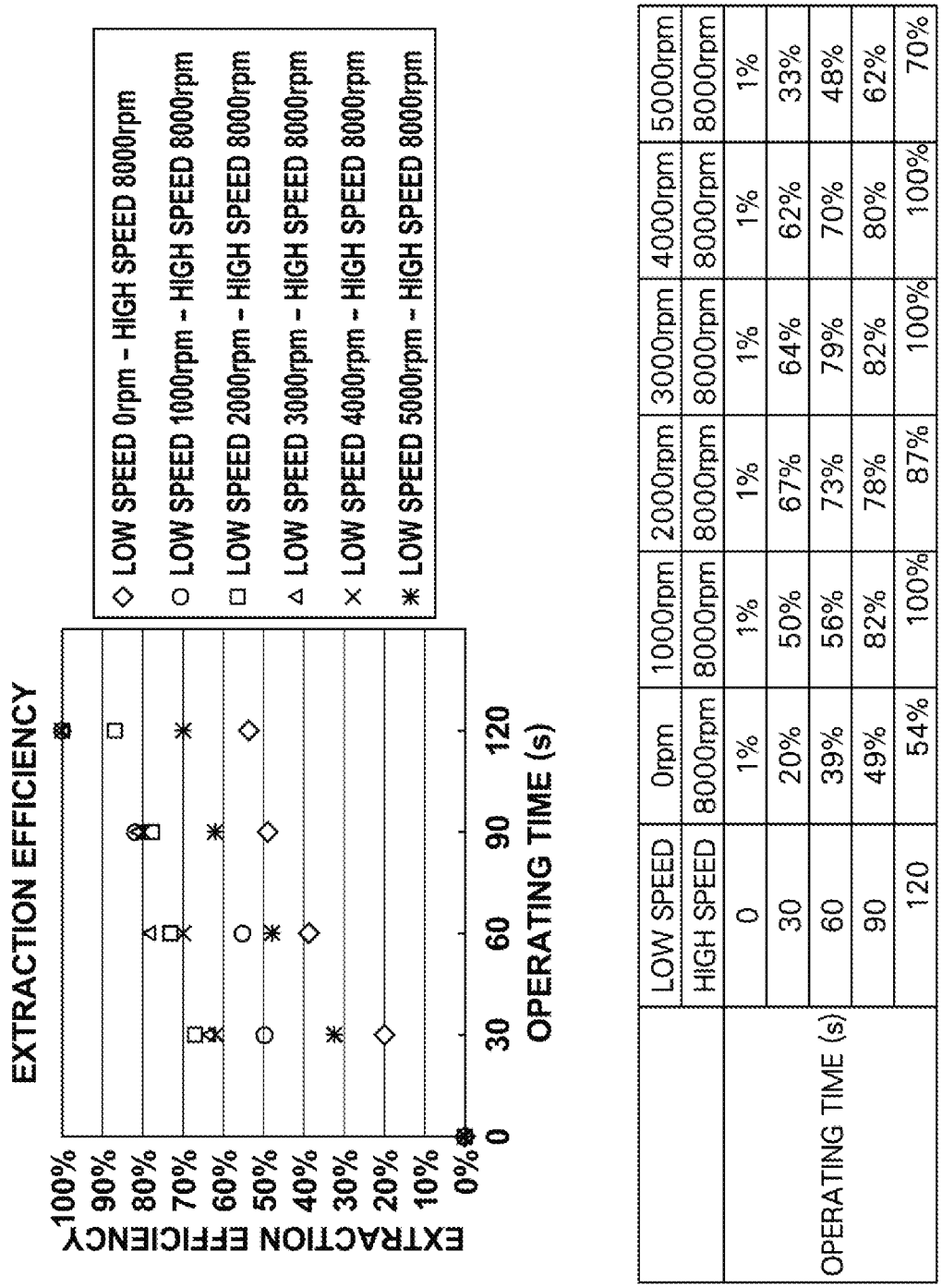
FIG. 13 is a data diagram that illustrates disruption results of a specimen by the specimen disrupting apparatus of the present disclosure (part 2).

FIG. 12 and FIG. 13 are data charts showing the values of qPCR quantitative values (%) with respect to the numbers of added spores. FIG. 12 shows data for a case in which the low rotational speed was set to 3000 rpm and the high rotational speed was changed from 6000 rpm to 10000 rpm in increments of 1000 pm. In addition, FIG. 13 shows data in which the high speed rotational speed was set to 8000 rpm and the low rotational speed was changed from 1000 rpm to 5000 rpm in increments of 1000 pm.

In addition, FIG. 12 also shows comparative data in which the low rotational speed rotation was set to 0 rpm and the high rotational speed was set to 3000 rpm. FIG. 13 also shows comparative data in which the low rotational speed was set to 0 rpm and the high rotational speed was set to 8000 rpm. In FIGS. 12 and 13, the rotation times of high speed rotation and low speed rotation are each 2.5 seconds, and data are shown for six cycles (30 seconds), 12 cycles (60 seconds), 18 cycles (90 seconds), and 24 cycles (120 seconds), with each cycle being 5 seconds long.

The comparative data of FIG. 12 shows data for six cycles (30 seconds), 12 cycles (60 seconds), 18 cycles (90 seconds), and 24 cycles (120 seconds), with 2.5 seconds of low speed rotation at 3000 rpm and 2.5 seconds of non rotation at 0 rpm as 1 cycle. The maximum qPCR quantitative value (%) is 13% after an operation time of 120 seconds.

In contrast, in the embodiment of the present disclosure, high qPCR quantitative values (%) are indicated for all of 30 seconds, 60 seconds, 90 seconds, and 120 seconds, compared with the same number of seconds in the case that low speed rotation at 3000 rpm and non rotation at 0 rpm were repeated. At operation times of 30 seconds or longer, the qPCR quantitative value (%) became 41% or greater by repeating low speed rotation at 3000 rpm and high speed rotation at 6000 rpm, the qPCR quantitative value (%) became 32% or greater by repeating low speed rotation at 3000 rpm and high speed rotation at 7000 rpm, the percentage of qPCR (%) became 64% or greater by repeating low speed rotation at 3000 rpm and high speed rotation at 8000 rpm, the qPCR quantification value (%) became 50% or greater by repeating low speed rotation at 3000 rpm and high speed rotation at 9000 rpm, the qPCR quantitative value (%) became 35% or greater by repeating low speed rotation at 3000 rpm and high speed rotation at 10000 rpm. That is, higher qPCR quantitative values (%) were realized in short amounts of time in all cases, compared to the maximum qPCR quantitative value (13%) in the case that low speed rotation at 3000 rpm and non rotation at 0 rpm were repeated.

The comparative data in FIG. 13 shows data for six cycles (30 seconds), 12 cycles (60 seconds), 18 cycles (90 seconds), and 24 cycles (120 seconds), with 2.5 seconds of high speed rotation at 8000 rpm and 2.5 seconds of non rotation at 0 rpm as 1 cycle. The maximum qPCR quantitative value (%) is 54% after an operation time of 120 seconds.

In contrast, in the embodiment of the present disclosure, high qPCR quantitative values (%) are indicated for all of 30 seconds, 60 seconds, 90 seconds, and 120 seconds, compared with the same number of seconds in the case that high speed rotation at 8000 rpm and non rotation at 0 rpm were repeated. At operation times of 60 seconds or longer, the qPCR quantitative value (%) became 56% or greater by repeating low speed rotation at 1000 rpm and high speed rotation at 8000 rpm. At operation times of 30 seconds or longer, the qPCR quantitative value (%) became 67% or greater by repeating low speed rotation at 2000 rpm and high speed rotation at 8000 rpm. At operation times of 30 seconds or longer, the percentage of qPCR (%) became 64% or greater by repeating low speed rotation at 3000 rpm and high speed rotation at 8000 rpm. At operation times of 30 seconds or longer, the qPCR quantification value (%) became 62% or greater by repeating low speed rotation at 4000 rpm and high speed rotation at 8000 rpm. That is, higher qPCR quantitative values (%) were realized in short amounts of time in all cases, compared to the maximum qPCR quantitative value (54%) in the case that high speed rotation at 8000 rpm and non rotation at 0 rpm were repeated.

The qPCR quantitative value (%) was 62% or greater at operation times of 90 seconds or longer when low speed rotation at 5000 rpm and high speed rotation at 8000 rpm were repeated. That is, a higher qPCR quantitative value was realized in a short amount of time, compared to the maximum qPCR quantitative value (54%) in the case that high speed rotation at 8000 rpm and non rotation at 0 rpm were repeated.

Figure 14:
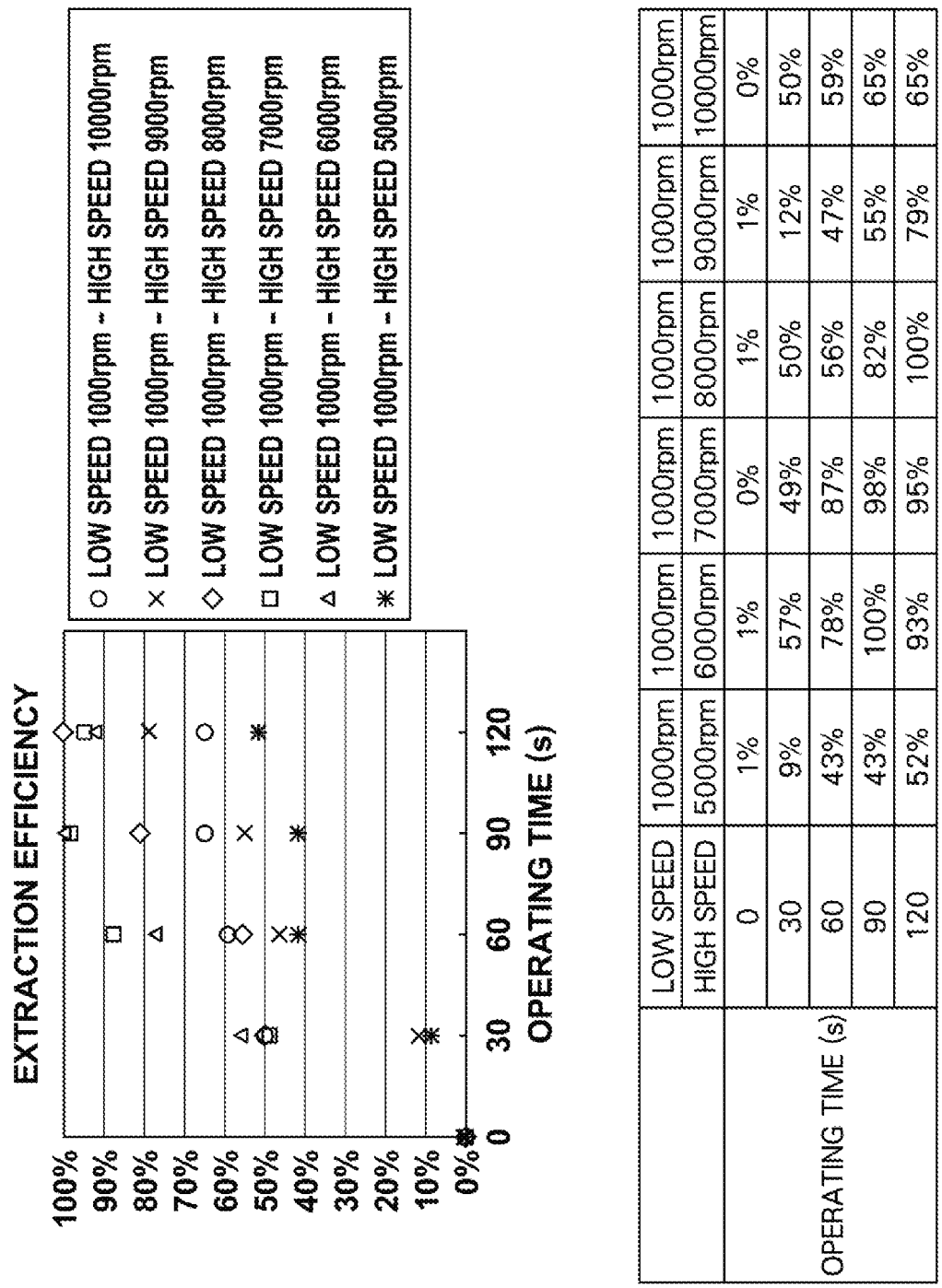
FIG. 14 is a data diagram that illustrates disruption results of a specimen by the specimen disrupting apparatus of the present disclosure (part 3).

FIG. 14 shows data for cases in which the low rotational speed is set to 1000 rpm and the high rotational speed is changed from 6000 rpm to 10000 rpm in increments of 1000 rpm. In addition, FIG. 14 also shows comparative data in which the low rotational speed is set to 1000 rpm and the high rotational speed is set to 5000 rpm. The rotation times of high speed rotation and low speed rotation are each 2.5 seconds, and data are shown for 6 repetitions (30 seconds), 12 repetitions (60 seconds), 18 repetitions (90 seconds), and 24 repetitions (120 seconds) of 5 second cycles.

The comparative data of FIG. 14 are those for 6 repetitions (30 seconds), 12 repetitions (60 seconds), 18 repetitions (90 seconds), and 24 repetitions (120 seconds) of 5 second cycles, in which each cycle includes 2.5 seconds of low speed rotation at 1000 rpm and 2.5 seconds of high speed rotation at 5000 rpm. The maximum qPCR quantitative value (%) is 52% at an operation time of 120 seconds. According to the results of FIG. 14, high qPCR quantitative values (%) are indicated for all of 30 seconds, 60 seconds, 90 seconds, and 120 seconds, compared with the same number of seconds in the case that low speed rotation at 1000 rpm and high speed rotation at 5000 rpm were repeated as described above. At operation times of 30 seconds or longer, the qPCR quantitative value (%) became 57% or greater by repeating low speed rotation at 1000 rpm and high speed rotation at 6000 rpm. At operation times of 60 seconds or longer, the qPCR quantitative value (%) became 87% or greater by repeating low speed rotation at 1000 rpm and high speed rotation at 7000 rpm. At operation times of 60 seconds or longer, the percentage of qPCR (%) became 56% or greater by repeating low speed rotation at 1000 rpm and high speed rotation at 8000 rpm. At operation times of 90 seconds or longer, the qPCR quantification value (%) became 55% or greater by repeating low speed rotation at 1000 rpm and high speed rotation at 9000 rpm. At operation times of 60 seconds or longer, the qPCR quantification value (%) became 59% or greater by repeating low speed rotation at 1000 rpm and high speed rotation at 10000 rpm. That is, higher qPCR quantitative values (%) were realized in short amounts of time in all cases, compared to the maximum qPCR quantitative value (52%) in the case that low speed rotation at 1000 rpm and high speed rotation at 8000 rpm were repeated.

Figure 15:
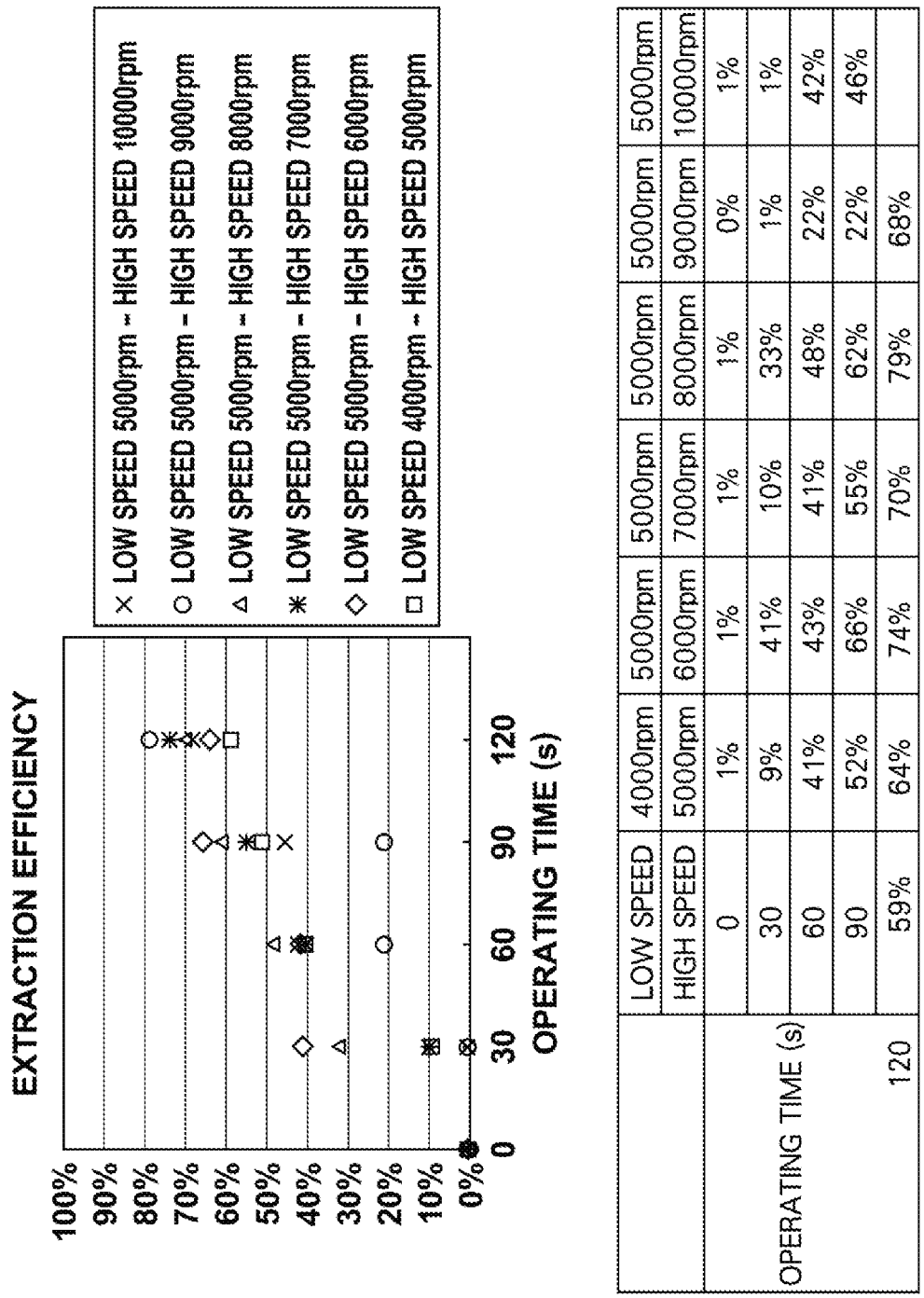
FIG. 15 is a data diagram that illustrates disruption results of a specimen by the specimen disrupting apparatus of the present disclosure (part 4).

FIG. 15 shows data for cases in which the low rotational speed is set to 5000 rpm and the high rotational speed is changed from 6000 rpm to 10000 rpm in increments of 1000 rpm. In addition, FIG. 15 also shows comparative data in which the low rotational speed is set to 4000 rpm and the high rotational speed is set to 5000 rpm. The rotation times of high speed rotation and low speed rotation are each 2.5 seconds, and data are shown for 6 repetitions (30 seconds), 12 repetitions (60 seconds), 18 repetitions (90 seconds), and 24 repetitions (120 seconds) of 5 second cycles.

The comparative data of FIG. 15 are those for 6 repetitions (30 seconds), 12 repetitions (60 seconds), 18 repetitions (90 seconds), and 24 repetitions (120 seconds) of cycles, in which each cycle includes 2.5 seconds of low speed rotation at 4000 rpm and 2.5 seconds of high speed rotation at 5000 rpm. The maximum qPCR quantitative value (%) is 59% at an operation time of 120 seconds. According to the results of FIG. 15, compared to the case in which low speed rotation at 4000 rpm and high speed rotation at 5000 rpm were repeated for 120 seconds, the qPCR quantitative value (%) became 66% or greater at operating times of 90 second or longer when low speed rotation at 5000 rpm and high speed rotation at 6000 rpm were repeated, the qPCR quantitative value (%) became 74% or greater at operating times of 120 seconds or longer when low speed rotation at 5000 rpm and high speed rotation at 7000 rpm were repeated, the qPCR quantitative value (%) became 62% or greater at operating times of 90 seconds or longer when low speed rotation at 5000 rpm and high speed rotation at 8000 rpm were repeated, the qPCR quantitative value (%) became 79% or greater at operating times of 120 seconds or longer when low speed rotation at 5000 rpm and high speed rotation at 9000 rpm were repeated, and the qPCR quantitative value (%) became 68% or greater at operating times of 120 seconds or longer when low speed rotation at 5000 rpm and high speed rotation at 10000 rpm were repeated. That is, higher qPCR quantitative values (%) were realized in short amounts of time in all cases, compared to the maximum qPCR quantitative value (59%) in the case that low speed rotation at 4000 rpm and high speed rotation at 5000 rpm were repeated.

The invention claimed is:

1. A specimen disrupting apparatus comprising:
a drive unit configured to cause a lower portion of a container containing a solution which includes a specimen, a great number of small diameter beads and a large diameter bead to rotate; and
a control unit configured to control the drive unit;
the control unit controlling the drive unit such that the lower portion of the container rotates at two or more different rotational speeds which change continuously, wherein the container comprises a lower rib in a vicinity of a bottom portion of an inner circumferential surface thereof that agitates the solution, and an upper rib at an upper portion of the inner circumferential surface thereof that causes the small diameter beads to bounce upward from the inner circumferential surface.

2. The specimen disrupting apparatus as defined in claim 1, wherein:
the control unit controls the drive unit such that a minimum rotational speed is within a range from 1000 rpm to 5000 rpm and a maximum rotational speed is within a range from 6000 rpm to 10000 rpm, among the two or more different rotational speeds at which the lower portion of the container is rotated.

3. The specimen disrupting apparatus as defined in claim 1, wherein:

a lower portion of the inner circumferential surface of the container is smooth such that the large diameter bead rolls on the lower inner circumferential surface during rotation.

4. The specimen disrupting apparatus as defined in claim 1, wherein:
the driving unit comprises:
a support member configured to support the upper portion of the container in a state in which the container is not rotatable about a central axis of the container;
a rotating member that rotates around a predetermined rotational axis; and
a connector for directly or indirectly connecting the lower portion of the container to the rotating member in a state where the central axis intersects with the rotational axis.

5. The specimen disrupting apparatus as defined in claim 4, wherein:
the angle at which the central axis intersects with the rotational axis is within a range from 2 to 5 degrees.

6. The specimen disrupting apparatus as defined in claim 4, wherein:
the support member comprises a flexible member having a hole therein, through which the upper portion of the container is inserted.

7. The specimen disrupting apparatus as defined in claim 6, wherein:
the flexible member comprises an annular portion, which is harder than the material of the flexible member, around the hole.

8. The specimen disrupting apparatus as defined in claim 6, wherein:
the support member further comprises a cylindrical container housing portion having an opening communicating with the hole of the flexible member and a bottom, wherein:
a convex portion is formed on the bottom of the container housing portion; and
a projection that engages with a rib formed on the outer peripheral surface of the container to prevent rotation of the container about the central axis thereof is formed on the inner circumferential surface of the flexible member.

9. The specimen disrupting apparatus as defined in claim 4, wherein:
the connector comprises one of a concave portion and a convex portion provided at a position remote from the rotational axis in the rotating member and one of a concave portion and a convex portion for engaging the concave portion or the convex portion, provided directly or indirectly at the lower end of the container.

10. A specimen disrupting apparatus comprising:
a plurality of drive units configured to cause a lower portion of a plurality of containers each containing a solution which includes a specimen, a great number of small diameter beads and a large diameter bead to rotate; and
a control unit configured to control the drive units;
the control unit controlling the drive units such that the lower portion of the containers rotates at two or more different rotational speeds which change continuously and
wherein the plurality of driving units rotate a plurality of the containers simultaneously, and the control unit controls the driving units such that when a portion of the containers among the plurality of containers are being rotated, the remaining containers are rotated at a different rotational speed from that of the portion of the containers.

11. A specimen disrupting method comprising:
storing a solution containing a specimen, a great number of small diameter beads, and a large diameter bead in a container; and
causing a lower portion of the container to rotate while continuously changing the rotational speed among two or more different rotational speeds, to disrupt the specimen with the beads,
wherein:
the large diameter bead is rolled on the inner circumferential surface at the lower portion of the container; and
the small diameter beads are moved in the vertical direction within the container in response to changes in the rotational speed.

12. The specimen disrupting method as defined in claim 11, wherein:
a minimum rotational speed is within a range from 1000 rpm to 5000 rpm and a maximum rotational speed is within a range from 6000 rpm to 10000 rpm, among the two or more different rotational speeds.

13. The specimen disrupting method as defined in claim 11, wherein:
the rotation is performed in a state where the central axis of the container intersects with the rotational axis about which the lower portion of the container rotates.

14. The specimen disrupting method as defined in claim 13, wherein:
the rotation is performed in a state in which the upper portion of the container is being supported.

15. The specimen disrupting method as defined in claim 13, wherein:
the angle at which the central axis intersects with the rotational axis is within a range from 2 to 5 degrees.

16. The specimen disrupting method as defined in claim 11, wherein:
a plurality of additional containers are prepared;
the solution, the great number of small diameter beads, and the large diameter bead is stored in each of the additional containers; and
the plurality of additional containers are rotated simultaneously.

17. The specimen disrupting method as defined in claim 16, wherein:
the plurality of containers, including the container and the additional containers, are divided into two groups; and
while the lower portions of the containers which belong to a first group are being rotated, the lower portions of the containers which belong to a second group are rotated at a rotational speed different from that of the first group.

* * * * *